(12) United States Patent
Adler, Jr. et al.

(10) Patent No.: US 9,314,160 B2
(45) Date of Patent: Apr. 19, 2016

(54) SYSTEMS AND METHODS FOR REAL-TIME TARGET VALIDATION FOR IMAGE-GUIDED RADIATION THERAPY

(71) Applicant: VARIAN Medical Systems, Inc., Palo Alto, CA (US)

(72) Inventors: John Rodenbeck Adler, Jr., Stanford, CA (US); Jianing Shi, Houston, TX (US); James E. Clayton, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 631 days.

(21) Appl. No.: 13/691,502

(22) Filed: Nov. 30, 2012

(65) Prior Publication Data

US 2013/0188856 A1 Jul. 25, 2013

Related U.S. Application Data

(60) Provisional application No. 61/565,900, filed on Dec. 1, 2011.

(51) Int. Cl.

| | |
|---|---|
| *G06K 9/00* | (2006.01) |
| *A61B 5/00* | (2006.01) |
| *A61B 6/12* | (2006.01) |
| *A61B 6/00* | (2006.01) |
| *A61N 5/10* | (2006.01) |
| *A61B 6/02* | (2006.01) |

(52) U.S. Cl.
CPC ............... *A61B 5/0033* (2013.01); *A61B 6/12* (2013.01); *A61B 6/463* (2013.01); *A61B 6/466* (2013.01); *A61N 5/107* (2013.01); *A61N 5/1049* (2013.01); *A61N 5/1064* (2013.01); *A61N 5/1067* (2013.01); *A61B 6/025* (2013.01); *A61N 2005/1062* (2013.01)

(58) Field of Classification Search
CPC .......... G06T 2207/10116; G06T 2207/10072; G06T 2207/10081; G06T 2207/10088; G06T 2207/10104; G06T 2207/10121; G06T 2207/10124; G06T 2207/10132; G06T 17/10; A61N 2005/0626; A61N 5/103; A61N 5/1064; A61N 5/1071
See application file for complete search history.

(56) References Cited

U.S. PATENT DOCUMENTS

| | | | | |
|---|---|---|---|---|
| 8,406,844 | B2* | 3/2013 | Ruchala et al. | 600/407 |
| 8,913,716 | B2* | 12/2014 | Sobering et al. | 378/65 |
| 2005/0049477 | A1* | 3/2005 | Fu et al. | 600/407 |
| 2007/0189591 | A1* | 8/2007 | Lu et al. | 382/128 |
| 2008/0002809 | A1* | 1/2008 | Bodduluri | 378/41 |
| 2008/0144908 | A1* | 6/2008 | West et al. | 382/131 |
| 2009/0163799 | A1* | 6/2009 | Erbel et al. | 600/424 |
| 2009/0180678 | A1* | 7/2009 | Kuduvalli et al. | 382/132 |
| 2010/0183196 | A1* | 7/2010 | Fu et al. | 382/103 |
| 2013/0114872 | A1* | 5/2013 | Chen et al. | 382/131 |

OTHER PUBLICATIONS

Osher et al ("Fast Linearized Bregman Iteration for Compressive Sensing and Sparse Denoising", 2008).*
Hissoiny et al. "GPUMCD: A new GPU-Oriented Monte Carlo dose calculation platform", Physics. med-ph, Jan. 6, 2011.

(Continued)

*Primary Examiner* — Avinash Yentrapati
(74) *Attorney, Agent, or Firm* — Shapiro, Gabor and Rosenberger, PLLC

(57) ABSTRACT

Systems and methods for real-time target validation during radiation treatment therapy based on real-time target displacement and radiation dosimetry measurements.

49 Claims, 15 Drawing Sheets

(56) References Cited

OTHER PUBLICATIONS

Lo et al. "Hardware acceleration of a Monte Carlo simulation for photodynamic therapy treatment planning", Journal of Biomedical Optics, Jan./Feb. 2009, vol. 14(1).

Dong et al "An Image Correlation Procedure for Digitally Reconstructed Radiographs and Electronic Portal Images", Int. J. Radiation Oncology Biol. Phys., vol. 33, No. 5, pp. 1053-1060, 1995.

\* cited by examiner

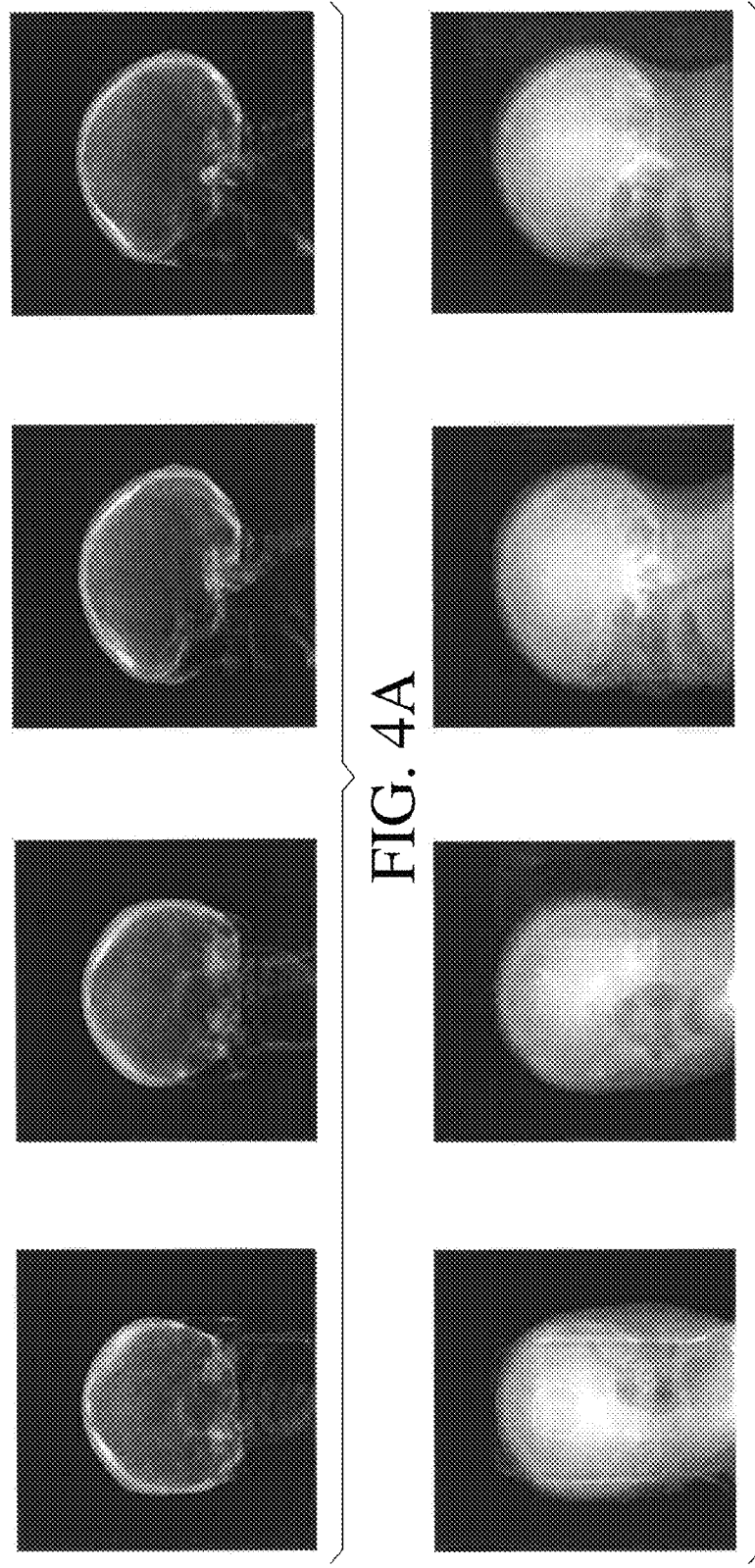

FIG. 14B $y$     $\Phi$     $x$ $M \times 1$     $M \times N \ (M < N)$     $N \times 1$

SYSTEMS AND METHODS FOR REAL-TIME TARGET VALIDATION FOR IMAGE-GUIDED RADIATION THERAPY

RELATED APPLICATIONS

This application claims the benefit of U.S. Provisional Application No. 61/565,900 filed Dec. 1, 2011, the content of which is hereby incorporated by reference in its entirety.

FIELD

The present disclosure relates generally to delivering radiation to a treatment target, and more particularly to systems, methods, and computer program products for real-time target validation during image-guided radiation therapy treatment.

BACKGROUND

Radiosurgery and radiotherapy systems are radiation therapy treatment systems that use external radiation beams to treat pathological anatomies (tumors, lesions, vascular malformations, nerve disorders, etc.) by delivering prescribed doses of radiation (X-rays, gamma rays, electrons, protons, and/or ions) to the pathological anatomy while minimizing radiation exposure to the surrounding tissue and critical anatomical structures. Radiotherapy is characterized by a low radiation dose per fraction (e.g., 100-200 centiGray), shorter fraction times (e.g., 10-30 minutes per treatment), and hyper fractionation (e.g., 30-45 fractions), and repeated treatments. Radiosurgery is characterized by a relatively high radiation dose per fraction (e.g., 500-2000 centiGray), extended treatment times per fraction (e.g., 30-60 minutes per treatment), and hypo-fractionation (e.g. 1-5 fractions or treatment days). Due to the high radiation dose delivered to the patient during radiosurgery, radiosurgery requires high spatial accuracy to ensure that the tumor or abnormality (i.e., the target) receives the prescribed dose while the surrounding normal tissue is spared.

In general, radiosurgery treatments consist of several phases. First, a precise three-dimensional (3D) map of the anatomical structures in the area of interest (head, body, etc.) is constructed using any one of (or combinations thereof) a computed tomography (CT), cone-beam CBCT, magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. Second, a motion path for the radiation beam is computed to deliver a dose distribution that the surgeon finds acceptable, taking into account a variety of medical constraints. During this phase, a team of specialists develop a treatment plan using special computer software to optimally irradiate the tumor and minimize dose to the surrounding normal tissue by designing beams of radiation to converge on the target area from different angles and planes. Third, the radiation treatment plan is executed. During this phase, the radiation dose is delivered to the patient according to the prescribed treatment plan.

To help deliver radiation therapy to the target according to the radiation treatment plan, image-guided radiation therapy (IGRT) can be used. IGRT is a radiation therapy process that uses cross-sectional images of a patient's internal anatomy taken during the radiation therapy treatment session (i.e., in-treatment images) to provide information about the patient's position. IGRT is thus a process of frequent two or three-dimensional imaging during the course of the radiation treatment used to direct the therapeutic radiation utilizing the imaging coordinates of the actual radiation treatment plan. This ensures that the patient is localized in the radiation treatment system in the same position as planned, and that the patient is properly aligned during the treatment. The IGRT imaging process is different from the imaging process used to delineate targets and organs in the planning process of radiation therapy (i.e., different from the pre-treatment images obtained during the first phase). Although, the IGRT process involves conformal radiation treatment guided by specialized imaging tests taken during the first phase, it does rely on the imaging modalities from the planning process as the reference coordinates for localizing the patient during treatment. Thus, associated with each image-guided radiation therapy system is an imaging system to provide in-treatment images that are used to set-up the radiation delivery procedure.

In-treatment images can include one or more two or three-dimensional images (typically X-ray) acquired at one or more different points of view during treatment. There are a variety of ways to acquire the in-treatment images. In certain approaches, distinct independent imaging systems and/or imaging methods are used for acquiring pre-treatment and in-treatment images, respectively. For example, a 3D IGRT could include localization of a cone-beam computed tomography (CBCT) dataset with a planning computed tomography (CT) dataset, and a 2D IGRT could include matching planar kilovoltage (kV) radiographs or megavoltage (MV) images with digital reconstructed radiographs (DRRs) obtained from the planning CT. Alternatively, another approach is to use portal imaging systems. In portal imaging systems, a detector is placed opposite the therapeutic radiation source to image the patient for setup and in-treatment images. Another approach is X-ray tomosynthesis which is an in-treatment imaging modality for use in conjunction with radiation treatment systems. X-ray tomosynthesis is a process of acquiring a number of two-dimensional X-ray projection images of a target volume using X-rays that are incident upon the target volume at respective number of different angles, followed by the mathematical processing of the two-dimensional X-ray projection images to yield a set of one or more tomosynthesis reconstruction images representative of one or more respective slices of the target volume.

In image-guided radiotherapies, there are many factors that can contribute to differences between the prescribed radiation dose distribution and the actual dose delivered (i.e., the actual dose delivered to the target during the radiation treatment). One such factor is uncertainty in the patient's position in the radiation therapy system. Other factors involve uncertainty that is introduced by changes that can occur during the course of the patient's treatment. Such changes can include random errors, such as small differences in a patient's setup position. Other sources are attributable to physiological changes that might occur if a patient's tumor regresses or if the patient loses weight during therapy. Another category of uncertainty includes motion. Motion can potentially overlap with either of the categories as some motion might be more random and unpredictable, whereas other motion can be more regular. These uncertainties can affect the quality of a patient's treatment and the actual radiation dose delivered to the target.

In existing radiosurgery therapy systems, establishing precision of therapeutic dose delivery is done by carefully calibrating the position and orientation of a well characterized imaging system with respect to the therapeutic radiation beam used during the treatment. The accuracy of the radiosurgery is, therefore, dependent on the fidelity with which this calibration process if performed.

In stereotactic radiosurgery (SRS), which is a highly precise form of radiation therapy used to treat tumors and abnormalities of the brain, 3D imaging, such as CT, MRI, and PET/CT, is used to generate pre-treatment images to locate the tumor or abnormality within the body and define its exact size and shape. SRS also relies on systems to immobilize and carefully position the patient's head during the initial imaging phase (pre-treatment imaging) as well as during the radiation therapy session. Therefore, in SRS, the pre-treatment images show the exact location of the tumor in relation to the head frame. In stereotactic radiosurgery, this calibration can utilize rigid external frame-based head immobilization which, when properly calibrated, reliably locates the head or other body parts in a known position with respect to the therapeutic beams. However, if the calibration is done incorrectly or if post pre-treatment imaging the head slips inside the external frame or the radiosurgery instrument is knocked out of alignment after calibration, a user may not know, and serious consequences are possible.

In the existing radiation therapies, therefore, radiation delivery is made based on the assumption that the radiation treatment plan was developed based on correct information, the position of the radiation beam relative to the patient set-up is correctly calibrated, and that the radiation therapy system not only functions properly but that it also functions based on correct and consistent external inputs used to program the system. However, if the calibration of the support device, for example, is incorrect, or the radiation therapy system functions improperly, or the treatment plan may include incorrect information, an incorrect dose will be delivered to the target during treatment even if the radiation therapy system operates as instructed.

Also, radiation therapy detectors typically are either not designed to detect high energy therapeutic beams or not designed to be constantly operating during radiosurgery, and therefore real-time validation of the target treatment volume is not feasible.

SUMMARY

The accuracy in delivering a predicted radiation dose to a target based on a predetermined treatment plan plays an important role in the ultimate success or failure of the radiation treatment. Inaccurate dose delivery can result in either insufficient radiation for cure, or excessive radiation to nearby healthy tissue. Therefore, validating in real-time that the predicted radiation dose is delivered to the actual treatment target volume according to the treatment plan is desirable.

The present disclosure includes systems, methods, and computer program products for confirming in real-time that a therapeutic beam in a radiation therapy system is delivered to the intended target.

The present disclosure also provides systems, methods, and computer program products for validating the target in real-time during image-guided radiosurgery.

The present disclosure also provides systems, methods, and computer program products for real-time target validation during radiation treatment therapy based on real-time target displacement and radiation dosimetry measurements.

The present disclosure also provides systems, methods, and computer program products for corroborating in real-time the spatial position and orientation of the actual treatment target volume with respect to the pretreatment planning target volume.

The present disclosure also provides systems, methods, and computer program products that serve as quality assurance tools for the accuracy of radiosurgery in real-time, and to allow surgeons to interrupt the surgery to recalibrate the system during the treatment.

In various embodiments, the systems, methods and computer program products include means for real-time target validation based on a determination of a three-dimensional (3D) path of the radiation penetrating the target and the amount of delivered therapeutic radiation dose.

In various embodiments, the real-time validation process includes determining the three-dimensional (3D) path of the radiation penetrating the target based on transmitted radiation intensity measurements.

BRIEF DESCRIPTION OF THE DRAWINGS

The drawings described herein are for illustration purposes only and are not intended to limit the scope of the present disclosure in any way. The invention will be best understood by reading the ensuing specification in conjunction with the drawing figures, in which like elements are designated by like reference numerals. As used herein, various embodiments can mean some or all embodiments.

FIG. 4A illustrates a library of (keV) synthesized DRRs according to various embodiments;

FIG. 4B illustrates a library of (MeV) synthesized DRRs according to various embodiments;

FIG. 14B illustrates a design matrix $\Phi$ for a collection of linear projections for volume reconstruction.

DETAILED DESCRIPTION

Figure 1A:
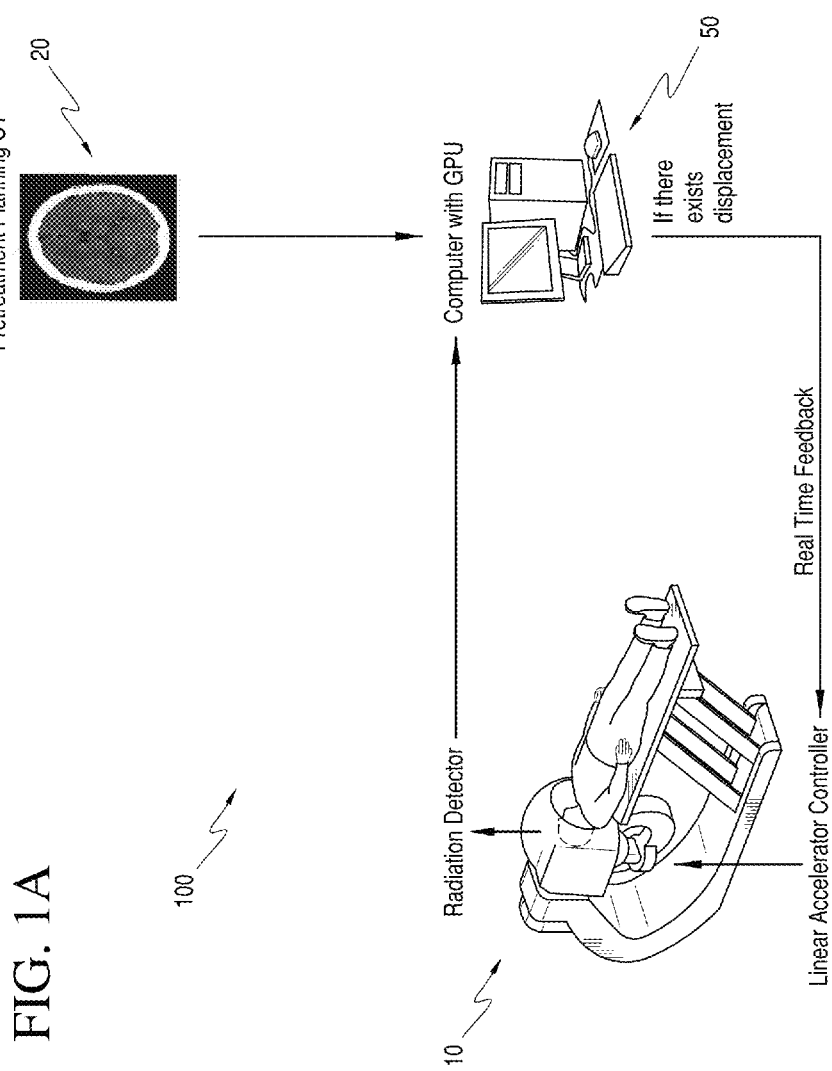
FIGS. 1A and 1B are perspective views of a radiation therapy system according to an embodiment of the invention.

Real-time validation according to various embodiments can include real-time displacement detection, real-time target volume reconstruction, real-time feedback, and real-time dosimeter monitoring. The displacement detection, the target volume reconstruction, and the dosimeter monitoring functions are based on computational algorithms incorporating transmitted therapeutic radiation trajectory and radiation fluence (i.e., energy per unit area) measurements.

Displacement detection is performed to ascertain any displacement of a therapeutic radiation beam with respect to the target. This detection can be obtained, for example, by correlating a previously generated and stored library of projection images of predicted beam trajectories with live projection images of beam trajectories obtained during radiation treatment. The live and the stored projection images can include radiation fluence information. During displacement detection, a comparison of the predicted radiation fluence from the library of predicted beam trajectories and the actual measured radiation fluence can be made to compute similarity measures between the two sets of fluences.

Real-time target volume reconstruction is performed to reconstruct a 3D target volume which is actually targeted by the therapeutic radiation beam. Such information can in real-time confirm to the operator that the treatment is being executed as planned. This can be done using reconstruction algorithms which use information based on the obtained projection images, the transmitted radiation fluence, and the geometry of the targeting device, and as explanatory variables the positions and orientations of the therapeutic beam. Parallel computing architectures may be used to accelerate the computation.

Real-time dosimetry is performed to compare in real-time the actual dose delivered to the target during the radiation treatment and the planned radiation dose. This comparison provides added quality assurance that the treatment therapy is being properly administered.

Real-time feedback is performed to correct the position of the therapeutic beam in real-time should any displacement of the target be determined or recorded. The feedback is triggered by a detected displacement signal being above a threshold displacement signal. The detected displacement signal is obtained by comparing the library of predicted projection images with the in-treatment image X-ray fluence information, and/or by comparing the in-treatment dosimetry measurement with previously recorded dosimetry measurements. If the detected displacement signal is larger than a predetermined threshold displacement signal, or if the detected dose is significantly larger than a prescribed dose, the feedback signal can automatically cause the radiation treatment to stop or can indicate to a medical personnel (e.g., surgeon) that the radiation delivery is not as planned and allow the medical personnel to stop the radiation treatment. This gives the operating surgeon the option to stop the treatment or surgery and to recalibrate the radiation treatment device or the treatment procedure accordingly.

Figure 1B:
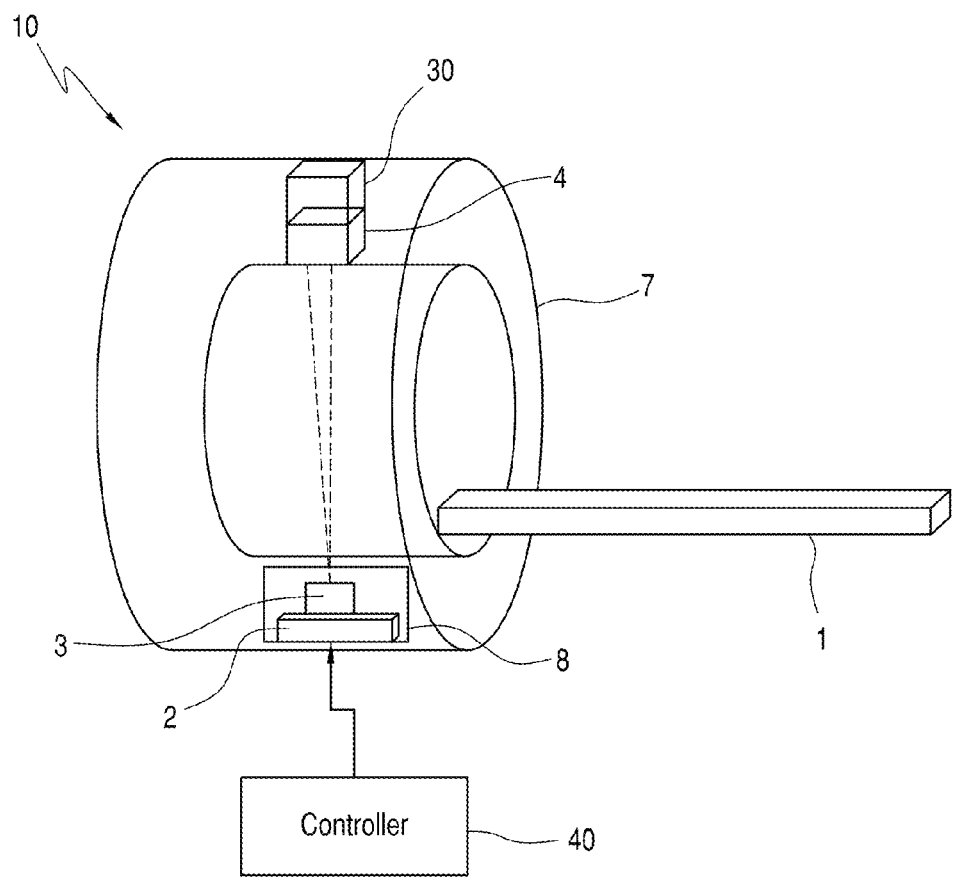

FIGS. 1A and 1B illustrate an exemplary radiation therapy treatment system 100 that can provide radiation therapy to a patient 5 and provide real-time target validation. The radiation therapy treatment can include photon-based radiation therapy, particle therapy, electron beam therapy, or any other type of treatment therapy. In an embodiment, the radiation therapy treatment system 100 includes a radiation treatment device 10, such as, but not limited to, a radiosurgery device, which can include a gantry 7 supporting a radiation module 8 which includes one or more radiation sources 3 and a linear accelerator 2 operable to generate a beam of kV or MV X-ray radiation. The gantry 7 can be a ring gantry (i.e., it extends through a full 360 degree arc to create a complete ring or circle), but other types of mounting arrangements may also be employed. For example, a C-type, partial ring gantry, or robotic arm could be used. Any other framework capable of positioning the radiation module 8 at various rotational and/or axial positions relative to the patient 5 may also be used. The radiation source 3 can also travel in a non-circular path that does not follow the shape of the gantry 7. The radiation module 8 can also include a modulation device (not shown) operable to modulate the radiation beam as well as to direct a therapeutic radiation beam toward the patient 5 and toward a portion of the patient which is desired to be irradiated. The portion desired to be irradiated is referred to as the target or target region or a region of interest. The patient 5 may have one or more regions of interest that need to be irradiated. A collimation device (not shown) may be included in the modulation device to define and adjust the size of an aperture through which the radiation beam may pass from the source 3 toward the patient 5. The collimation device may be controlled by an actuator (not shown) which can be controlled by a computer processing system 50 and/or a controller 40.

In an embodiment, the radiation therapy includes, but is not limited to, a kV or MV energy image-guided arc-type radiation therapy or radiosurgery, such as, but not limited to, stereotactic radiosurgery (SRS). The radiosurgery device 10 can be a self-shielded radiosurgery device, such as but not limited to, an arc-type X-ray image guided self-shielded radiosurgery device. Such a set-up enables the radiation sensor(s) 4 to be positioned directly opposite the therapeutic radiation source(s) 3 because it can be positioned outside specialized radiation bunkers. This setup makes it possible to continuously detect the therapeutic beam energy after it passes through the target volume.

To provide image-guidance, the radiosurgery device 10 includes an imaging device 30 for detecting and recording the transmission of the therapeutic X-ray beams from the source 3. The imaging device 30 can be a digital imaging device including a CMOS detector or an amorphous silicon detector or any other radiation detectors capable of receiving the therapeutic radiation that passes through the patient 5 and capable of measuring transmitted X-rays. These imaging devices can include, but are not limited to, segmented ion chambers, multiwire proportional counters, scintillating fibers, and Cerenkov detectors. The digital imaging device 30 can be positioned so that the detector 4 and the therapeutic radiation source 3 are arranged to be directly opposite from each other, and so that the detector 4 can continuously receive during the treatment the therapeutic radiation beams that passed through the target region of the patient 5. The imaging device 30 generally consists of picture elements (pixels) that register the amount of radiation that falls on them and that convert the received amount of radiation into a corresponding number of electrons. The electrons are converted into electrical signals which are further processed using either the imaging device 30 or the computer 50. Such a configuration (i.e., digital imaging detector(s) positioned opposite the therapeutic source(s)) provides the ability to capture in real-time the energy and intensity of the therapeutic radiation transmitted through the target volume and to generate two-dimensional (2D) in-treatment images of digitized X-ray measurements.

In an embodiment, a photodetector system with a scintillating fiber detector in connection with either a CCD camera, an a-Si TFT photodiode array, or a CMOS sensor, or any other device capable of producing a reproducible image with the level of light produced by the scintillating fiber, is used. The scintillating optical fibers function as small radiation detectors. These scintillating fibers can be distributed as desired within a three-dimensional detection space so as to gather radiation beam data, e.g., energy distribution within the space. The photodetector system includes an imager that converts the optical energy transmitted by the collection of optical fibers to an electric signal that may be thereafter converted to a radiation dose. The photo-detector imager can also take a 2D image of the input optical signals from the scintillating fibers.

Since each discrete therapeutic radiation beam that passes through the patient 5 carries with it a unique signature of the specific anatomy through which it passes, the detector 4 is operable to measure the intensity of the transmitted therapeutic radiation through the specific anatomy, the amount of radiation absorbed by the specific anatomy, and the trajectory of the beam through the anatomy. A precise analysis of the transmitted beams (beam trajectory) through the patient, together with a detector pixel by pixel measurement of the beam fluence (i.e., energy per unit area) allows for a determination of the three-dimensional (3D) path of therapeutic radiation penetrating a known object, when the radiation scatter of the anatomy in question is known. The radiation scatter of the anatomy in question can be determined by CT scanning, for example, prior to commencing the radiation therapy. The radiation scatter can be estimated based on knowledge of the CT number (Hounsfield unit HU) derived from previous or current scans. Knowing the 3D path of radiation that is delivered to the target volume during treatment allows for real-time determination of the spatial position and orientation of the actual treatment target volume, i.e., the actual volume of the target that is being irradiated during the treatment. Corroborating the spatial position and orientation of the actual treatment target volume in real-time with respect to the pretreatment planning target volume, i.e., the volume of the target planned during the planning phase, can validate the prescribed radiation treatment delivery. In addition, knowledge of the radiation dose delivered to the actual target volume in real-time can corroborate the radiation dose delivery treatment plan.

Generally, in radiosurgery, given the small volume of the targets (approximately 3 cm in diameter) and the greater penetration and less scatter of the megavolt (MV) therapeutic radiation, the resulting in-treatment images may have a limited field, poor resolution, and may be noisy, and therefore precise analysis of the transmitted beams can be difficult because at MV energies Compton Scattering is the dominant process until the energy of the photon beam is more than 10 MeV, whereas, at lower (keV) energies there is a competing mechanism, such as the photoelectric effect, to Compton Scattering. However, by using statistical measures and fast computational algorithms as described herein, embodiments can determine in real-time the 3D path of therapeutic radiation penetrating the treatment target volume, as well as the actual therapeutic dose delivered to the treatment target volume. The actual 3D path of therapeutic radiation penetrating the treatment target can also be corroborated with the prescribed 3D path, and therefore, real-time validation of the radiation delivery treatment plan can be achieved.

In operation, prior to radiation therapy treatment, a previously constructed model which embodies the 3D geometry of the patient and the linear accelerator and any additional hardware, such as, but not limited to, collimators, which are used as the final therapeutic radiation field defining devices, of the specific radiation treatment device 10 together with the patient's 5 anatomy is stored in a storage device in the computer 50. In order to generate a treatment plan, the patient 5 undergoing radiosurgery or radiotherapy treatment is imaged with diagnostic CT scanning, for example. Other forms of diagnostic scanning, such as, but not limited to, MRI can also be used. The CT scan provides pre-treatment images including a 3D Hounsfield map of the anatomy in question. Since most forms of radiosurgery require placement of a lightweight head frame (when the anatomy in question is the head) to help define the exact location of the tumor and to help immobilize the head so there is no movement during the treatment, the CT scan is done with the head frame on. A treatment planning module (shown in FIG. 12) can configure the computer 50 using specially designed planning software to precisely determine the treatment plan for the patient 5. Alternatively, the pre-treatment images and the treatment plan are developed externally and the information is transferred to the computer 50. Once the treatment plan is generated, the patient 5 is positioned on a sliding surgical bed 1 encircled by the linear accelerator 2. This subsequent position (bounded by certain approximations) of the constrained patient's anatomy (for example, the head with the head frame) within the radiosurgery device 10 can be estimated prior to radiosurgery.

Figure 3:
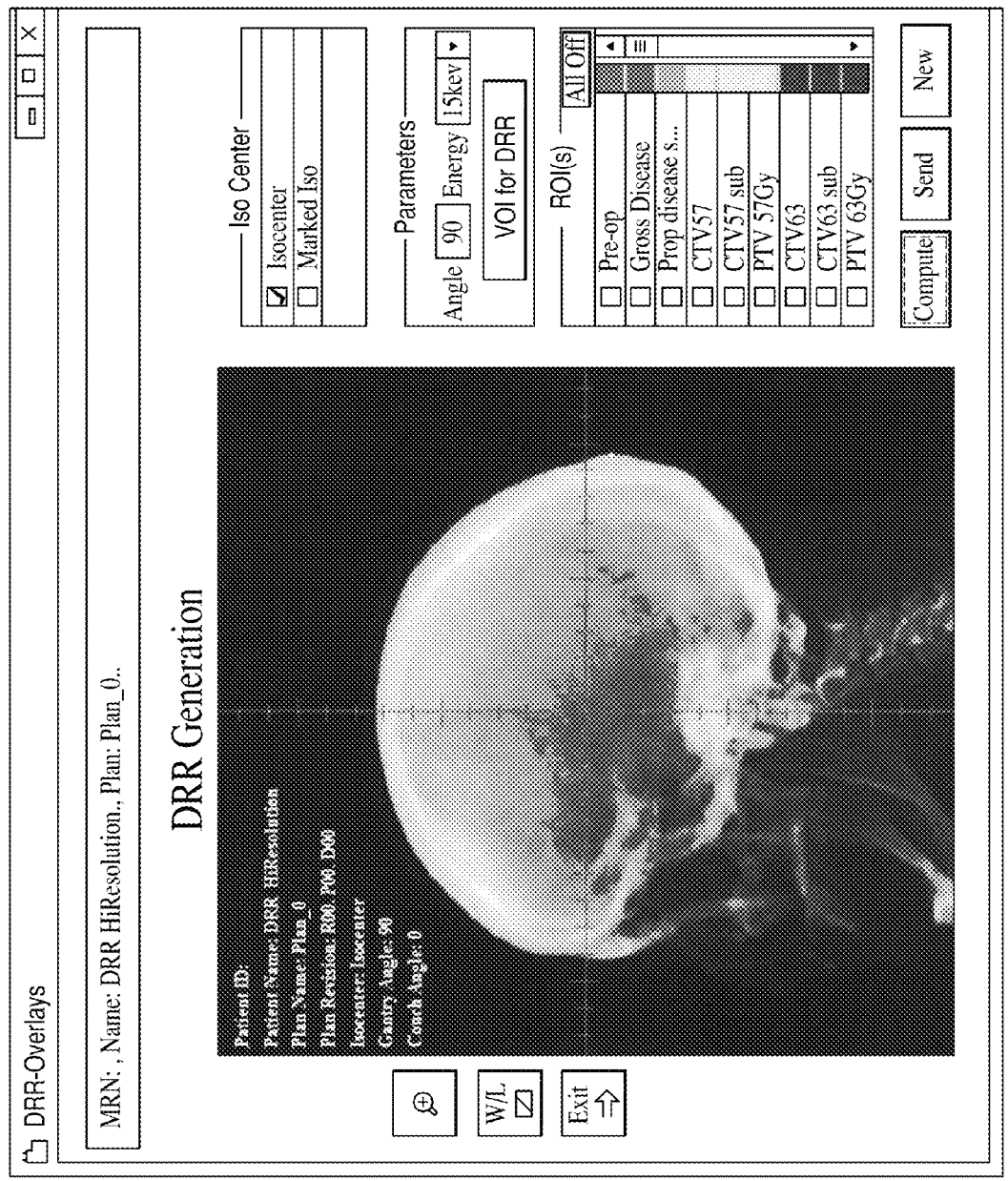
FIG. 3 is a schematic illustration of generating DRRs according to various embodiments.

The estimated position of the patient 5 anatomy within the radiosurgery device 10, combined with the previously stored 3D model of the patient along with the linear accelerator geometry and any additional hardware used in radiotherapy to define the therapeutic radiation field of the radiation treatment device 10, enable algorithms included in the analysis module (shown in FIG. 12) to predict the approximate trajectory of one or more treatment beams through the anatomy in question (or each of the treatment beam planned in the treatment plan). In order to generate the prediction, a library of digitally reconstructed radiographs (DRRs) is synthesized by simulating the projection of therapeutic beams at the targeted volume at different isocenters of radiation and different projection angles, as shown in FIG. 3, for example. One of the more rigorous methods by which projection images for individual beams can be synthesized is the Monte Carlo simulation for multi-layered media (MCML) method. The MCML method models how steady light transports in multi-layered media. It assumes infinitely wide layers and models an incident pencil beam that is perpendicular to the surface. The MCML approach scores absorption, reflectance, and transmittance of light in the tissue. The key steps in the MCML program are shown in the diagram of FIG. 13.

Each photon packet undergoes three steps, hop, drop, and spin that are repeated continuously in the simulation. The hop step moves the photon packets from a current position to the next interaction site by computing the step size through sampling a probability distribution based on the photon's free path. The drop step adjusts the photon packet's weight to simulate absorption based on the absorption coefficient at the site of the interaction. The spin step computes the scattering angle. When a photon exits the tissue through the top or bottom layer, it is terminated. If the photon weight has reached a threshold value, a survival roulette is performed to determine if tracking of the photon packet should end. If the photon survives, its weight is increased. Using this model, projection images for individual beams can be synthesized.

Taking advantage of the fact that the therapeutic beam has megavoltage (MeV) energy, which leads to little scattering, the MCML simulation can be simplified via ray tracking models which simulate primary radiation transmission only and do not consider any scattered radiation either from the patient's body or the collimator. In such models, the primary transmission I can be calculated by: $I = I_o R^{-2} \exp(-\int \mu dx)$, where $I_o$ is the incident fluence without attenuation, $\mu$ is the total linear attenuation coefficient, and R is the distance from the virtual source position to the point of calculation. This approximation method can be used to speed up the synthesizing process.

Parallel computing architectures, such as, but not limited to, GPU (graphic processing unit) and multi-core environment, or distributed computing with GPU clusters installed in different computers within a local area network (LAN), or parallel computing architecture with a cluster of servers within high-speed interconnect, can be employed to accelerate the simulation computation. The parallelization of the MCML model on parallel computing architectures can be done by employing an embarrassingly parallel computation where the MCML algorithm is kept intact and paralleled across an expanded search space of head positions and beam trajectories, or through divide and conquer parallelization which uses optimization inside the MCML model by minimizing divergent behavior due to photon-electron coupling, for example. These calculations can be performed over an expanded search space of head positions and beam trajectories, and the resulting images can be stored as synthetic DRR images in a look up table in the computer 50. FIG. 4 illustrates a library of DRRs obtained under different energy levels using the ray tracing method. FIG. 4A shows synthesized (keV) DRRs, and FIG. 4B shows synthesized (MeV) DRRs.

Also prior to the commencement of the radiation treatment, and prior to the positioning of the patient 5 on the surgical bed 1, a trial run or a cross check of the dose rates and positions of the device 10 for the prescribed radiation dose can be performed. The radiation dose prediction module uses this information to determine a baseline for radiation dosimetry during the treatment. Since the therapeutic beam assumes a specific shape based on the shape and size of the collimator present in the radiation therapy device 10, this shape information also provides a signature for the prescribed therapeutic treatment for each projection angle. The shape and dose distribution for each projection angle obtained during the cross check is stored in the computer 50 as a library of shape and dose distributions. This information can be used for real-time dosimetry monitoring during the treatment.

Figure 2:
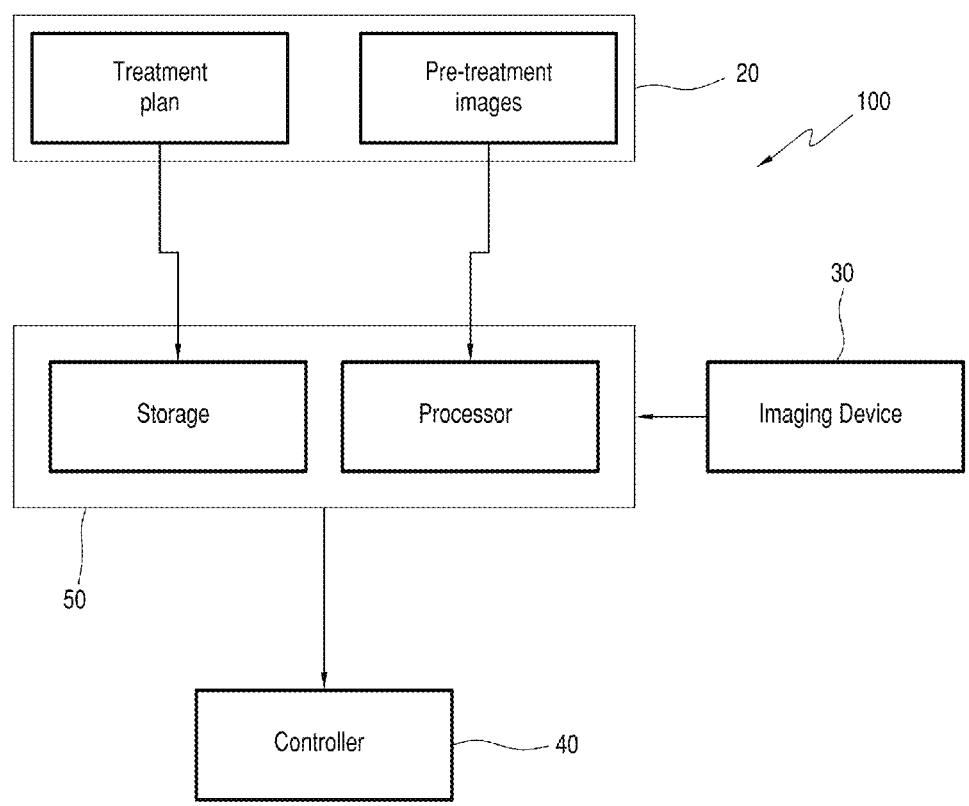
FIG. 2 is a schematic illustration of the radiation therapy system of FIG. 1.

FIG. 2 illustrates schematically the radiation treatment device 10 used for real-time validation. In operation, during the treatment session, namely, during delivery of the radiation therapy treatment according to the treatment plan, the detector(s) 4 in the digital imaging device 30 receives data from different projection angles $0 \le \theta \le 360°$ as the linear accelerator 2 rotates around the gantry 7 and emits therapeutic radiation toward the patient 5. The digital imaging device 30 collects in real time the transmitted energy and produces 2D digital images which represent two-dimensional arrays of digitized X-ray measurements. These live in-treatment images are sent to the computer 50 for further processing. In another embodiment, both, the live in-treatment images, as well as images obtained using an additional kV source (not shown) obtained are sent to the computer 50 for further processing.

In an embodiment, digital tomosynthesis is performed to generate the in-treatment images. To acquire the images, the therapeutic X-ray source 3 emits X-rays toward the target from a discrete number of angles during one sweep of the linear accelerator and produces a plurality of cross-sectional images which are reconstructed to produce images at different planes within the patient 5. The transmitted X-ray radiation is detected using a flat panel digital detector 4. Shift-and add (SAA) reconstruction algorithms and/or other applicable mathematical de-blurring techniques can be used to reconstructs the in-treatment images and to improve quality of the images.

Embodiments of the system 100 can include the computer 50 including typical hardware such as a processor, and an operating system for running various software programs and/or communication applications. The computer can include software programs that operate to communicate with the radiation therapy device 10, and the software programs are also operable to receive data from any external software programs and hardware. The computer 50 can also include any suitable input/output devices adapted to be accessed by medical personnel, as well as I/O interfaces, storage devices, memory, keyboard, mouse, monitor, printers, scanner, etc. The computer 50 can also be networked with other computers and radiation therapy systems 20. Both the radiation therapy device 10 and the computer 50 can communicate with a network as well as a database and servers. The computer 50 is also adapted to transfer medical image related data between different pieces of medical equipment.

Figure 12:
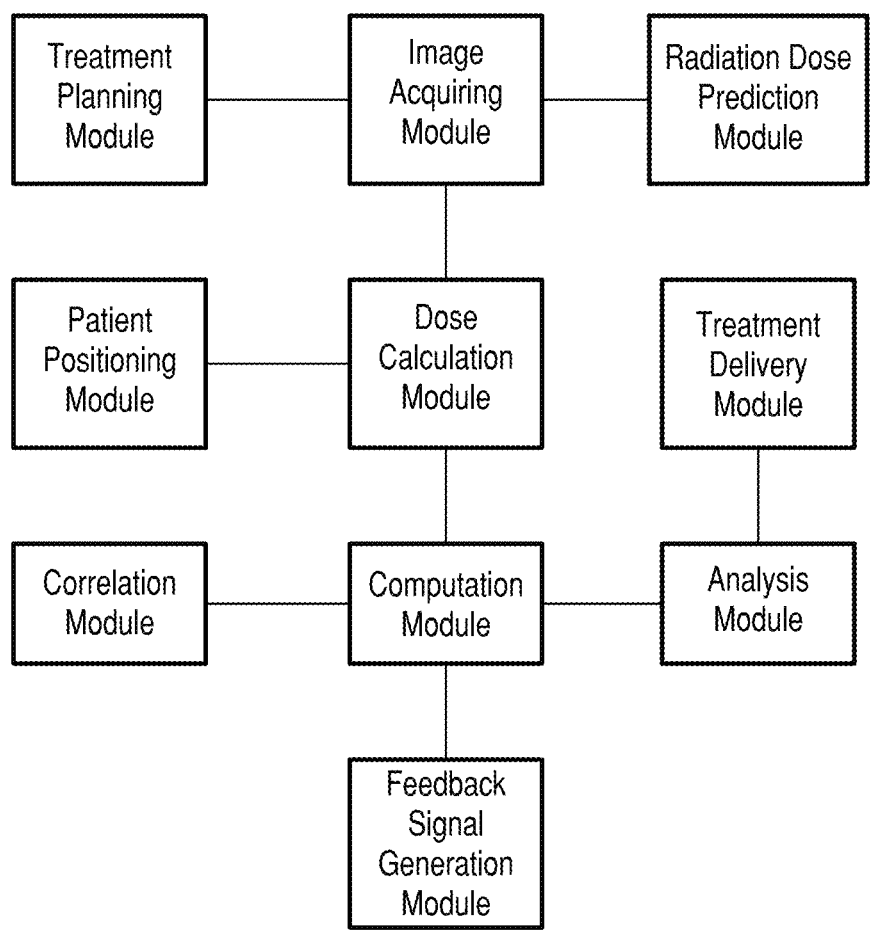
FIG. 12 is a schematic diagram of computer-based modules comprising a sequence of programmed instructions used in the radiation therapy treatment system of FIG. 1 to implement a real-time target validation process.
Figure 13:
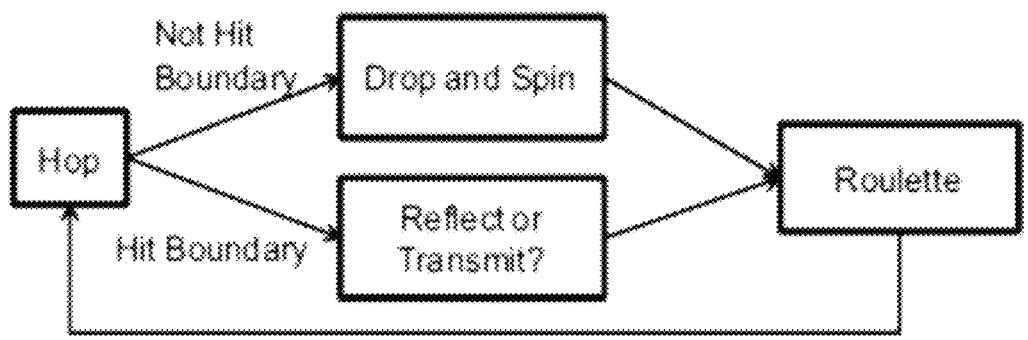
FIG. 13 illustrates a multi-layered media (MCML) simulation method.

The system 100 can also include a plurality of modules containing programmed instructions which, as shown in FIG. 12, communicate with each other and cause the system 100 to perform different functions related to radiation therapy/surgery, as discussed herein, when executed. For example, the system 100 can include a treatment plan module operable to generate the treatment plan for the patient 5 based on a plurality of data input to the system by the medical personnel, a patient positioning module operable to position and align the patient 5 with respect to the isocenter of the gantry 7 for a particular radiation therapy treatment, an image acquiring module operable to instruct the radiation therapy device (e.g., radiosurgery device) 10 to acquire images of the patient 5 prior to the radiation therapy treatment (i.e., pre-treatment images used for treatment planning and patient positioning) and/or during the radiation therapy treatment (i.e., in-treatment images), and to instruct other imaging devices or systems 20 to acquire images of the patient 5.

The system 100 can further include a radiation dose prediction module operable to predict a dose to be delivered to the patient 5 before commencement of the radiation treatment therapy, a dose calculation module operable to calculate the actual dose delivered to the patient 5 during radiation therapy treatment, a treatment delivery module operable to instruct the radiation therapy device 10 to deliver the treatment plan to the patient 5, a correlation module operable to correlate the DRRs with the in-treatment images obtained during radiation therapy, a computation module operable to reconstruct a three-dimensional target volume from in-treatment images, an analysis module operable to compute displacement measurements, and a feedback module operable to instruct the controller in real-time to stop radiation therapy based on a comparison of the calculated displacement with a predetermined threshold value (range). The modules can be written in the C or C++ programming language, for example.

Displacement Measurement

Upon receipt of the live in-treatment images, the correlation module in the computer 50 executes one or more algorithms to compare the live in-treatment images with the stored library of synthetic DRRs, and the correlation module executes one or more algorithms to compute similarity measures between the live images and the DRRs. Since the information contained in the live images are primarily due to bone structures (for instance the skull if the surgery is performed for treating a brain tumor) over a span of projection angles, the series of collected live images carry variations that constitute unique signatures of the skull thickness and curvatures. For example, the variation of collected live images over a span of projection angles will be different when such projections are focused over the thickest or thinnest part of the skull. Therefore, one parameter (metric) that can be estimated is the correlation between the live in-treatment images (i.e., live image series) and the synthesized DRRs over a span of projection angles. Variations in the anatomy, such as skull thickness, imaging geometry, tissue density, tissue type, tissue attenuation coefficients, tumor properties, etc., can also be utilized to generate similarity measures between synthesized DRRs and in-treatment images. These variations are effective indicators for detecting displacement. This type of similarity measurement is in the space of therapeutic fluence.

The correlation between these two sets of images, namely, the live in-treatment images and the synthesized DRRs, results in a statistical measure of correspondence. Based on the measured correspondence, a series of beam trajectories, and locations of the targeted energy between the two sets of images can be corroborated. A change in the correlation between the beam trajectories and locations of the targeted energy and the beam trajectories and energy locations in the DRRs indicates that the target is displaced. If the target displacement is larger than a certain predetermined threshold value, a stop signal is generated by the computation module and sent as a feedback signal to the controller 40, which upon receiving the feedback signal, can generate an output prompting the surgeon to optionally interrupt the radiosurgery, or the feedback signal can be used to automatically interrupt the radiosurgery. This process allows a surgeon to confirm the fidelity of radiosurgery during the procedure.

Figure 5A:
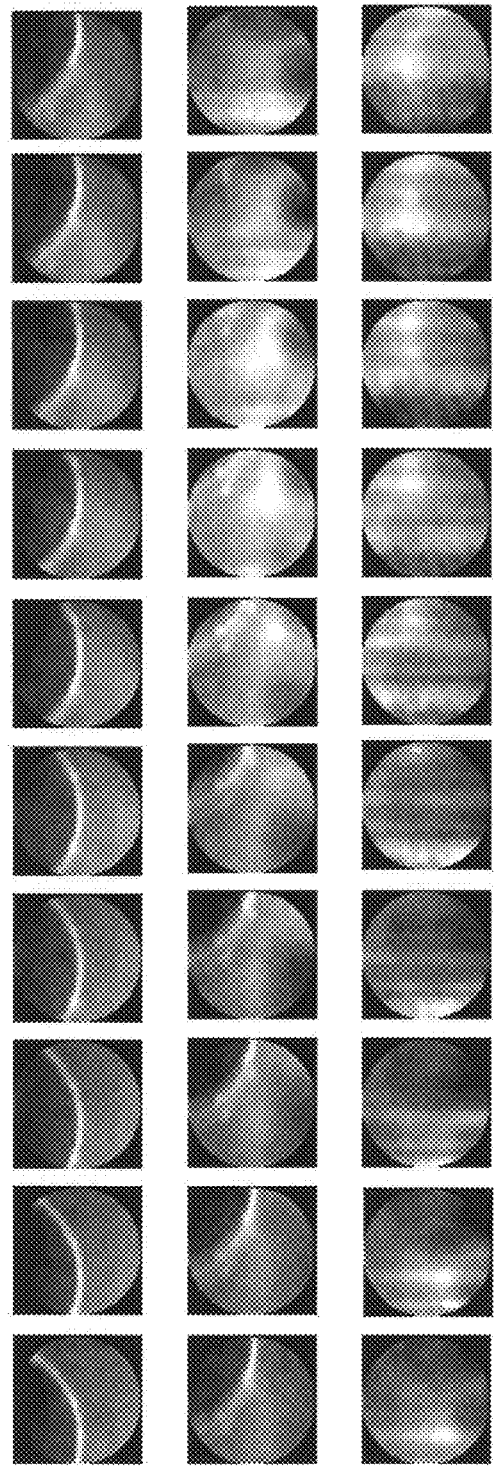
FIGS. 5A-5B illustrate a library of DRRs for different gantry angles.
Figure 5B:
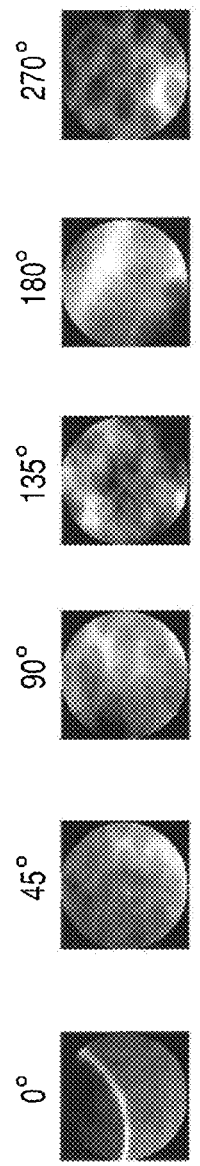
Figure 6:
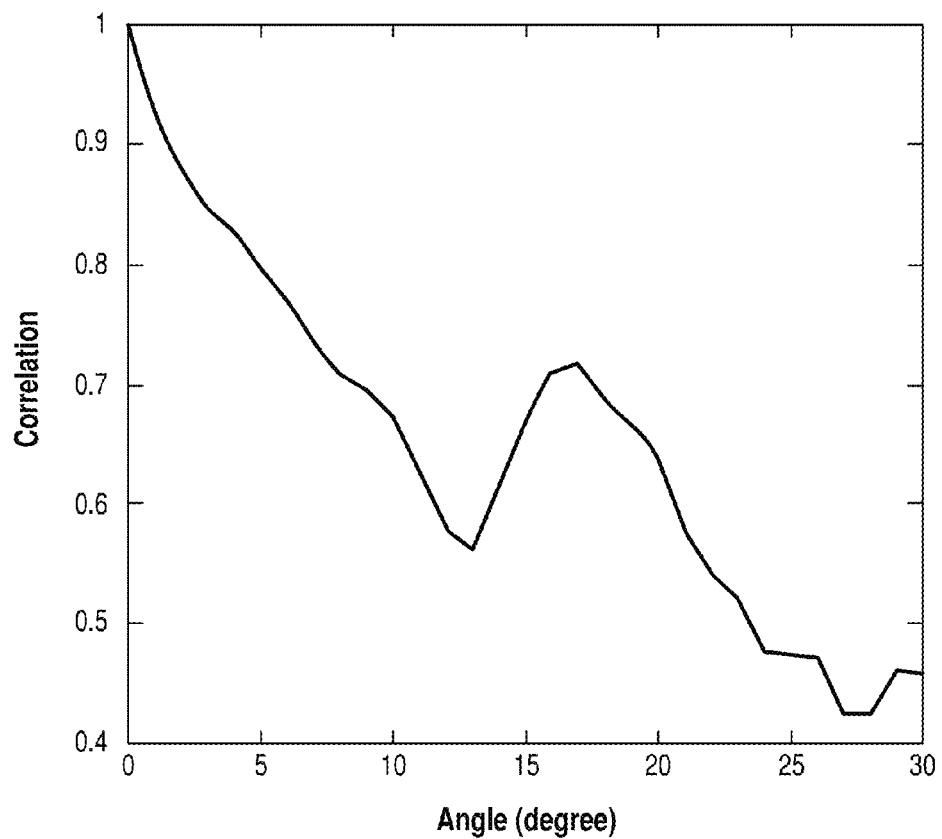
FIG. 6 illustrates a correlation graph between DRRs and live images at different gantry angles.

A library of synthesized DRRs obtained for different gantry angles (i.e., projection angles) is shown in FIGS. 5A-5B. FIG. 5A shows a library of synthesized DRRs for gantry angles spanning a range between 0-30° with a 1 degree increment (i.e., one DRR image for every angle between 0° and 30°), and FIG. 5B shows DRRs for projections at 0°, 45°, 90°, 135°, 180°, and 270°. The correlation over a series of projections angles between live in-treatment images obtained using a process as shown and described throughout the specification and the synthesized DRRs is shown in FIG. 6. A significant change in the correlation between the beam trajectories and locations of the targeted energy and the beam trajectories and energy locations in the DRRs can be seen in the graph. This is an indication that the target is displaced.

Figure 7B:
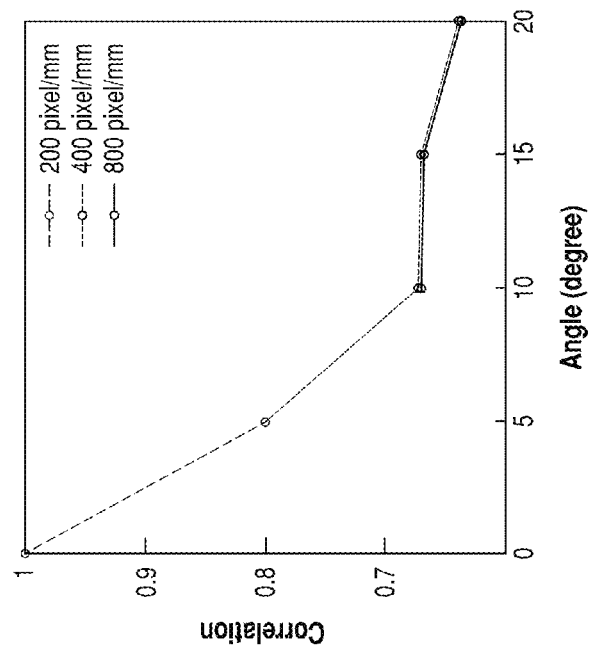
FIGS. 7A-7B illustrate correlation between detector resolution and displacement detection.
Figure 7A:
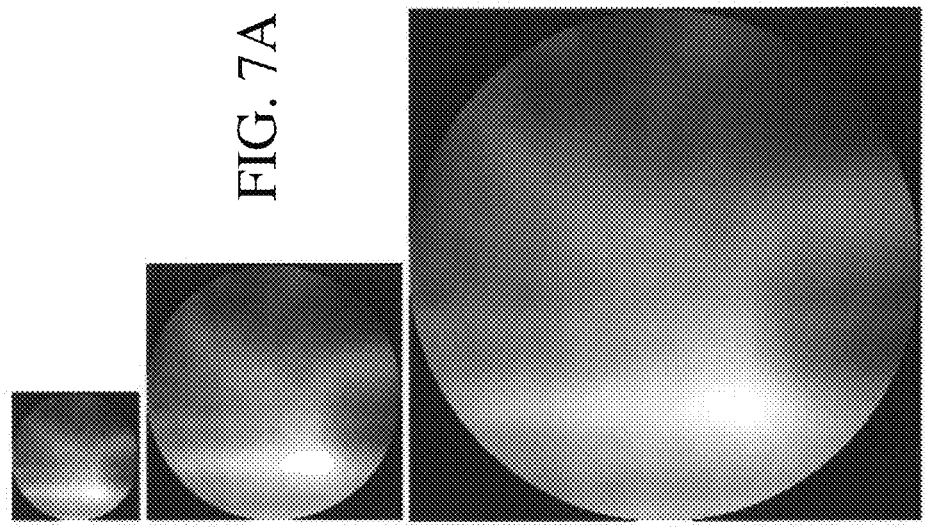

A study of the impact of detector resolution on displacement is shown in FIGS. 7A-7B. FIG. 7A illustrates three different images obtained using detectors having different resolutions, with the first detector having a resolution of 200 pixel/mm, the second detector a resolution of 400 pixel/mm, and a third detector a resolution of 800 pixel/mm. FIG. 7B illustrates that resolution has no significant impact on the displacement, and therefore, a detector with high resolution is not required for the purpose of displacement detection.

As an alternative to the therapeutic fluence space correlation metric described above, a compressive sensing algorithm can also be applied. While the correlation approach described above formulates the therapeutic beam as a forward problem, compressive sensing algorithm can cast it as an inverse problem. In the inverse problem, one can solve for an estimated thickness of the skull, for example, and then compute a correlation between the estimated and prescribed thicknesses. Thereby, the similarity measure will be cast back in a space of skull thickness (when the target is the brain tumor for instance), instead of the fluence space, using a compressive sensing algorithm.

The compressive sensing algorithm is designed to detect signal changes using incomplete and noisy measurements. This is beneficial because in order to validate a target in real time during radiosurgery, for example, one cannot afford to wait until the completion of the surgery to get enough samples (projection angles) for computation because by then it would be too late to correct the displacement and error. Since the objective is to validate the target in real-time, constructing meaningful quantities online using as fewer number of samples as possible is key. Therefore, an undersampled environment is present.

The essence of compressive sensing is to solve, in a linear system, for unknown variables using under-sampled measurements. Using this technique, in-treatment images using the therapeutic beam can be acquired over a span of projection angles as under-sampled measurements y, the transmittance over the therapeutic target can be modeled as design matrix $\Phi$, and solutions x for signatures of the skull (such as but not limited to, skull thickness and curvature) can be acquired. Specifically, since the under-sampled measurements are sparse in the space of projection angles, sparsity can be modeled using a convex form of a sparse promoting norm, such as an L1 norm, and the linear system can be solved for the convex optimization problem. Since the image signatures are piece-wise constant, total variation (TV) can be employed as a type of structured sparsity to enhance the quality of the algorithm. In addition, theoretical guarantees for the minimum number of projection angles to detect signal changes can be predicted. This form of compressive sensing tackles the problem of solving an underdetermined linear system, with fewer samples compared to unknowns.

Figure 14A:
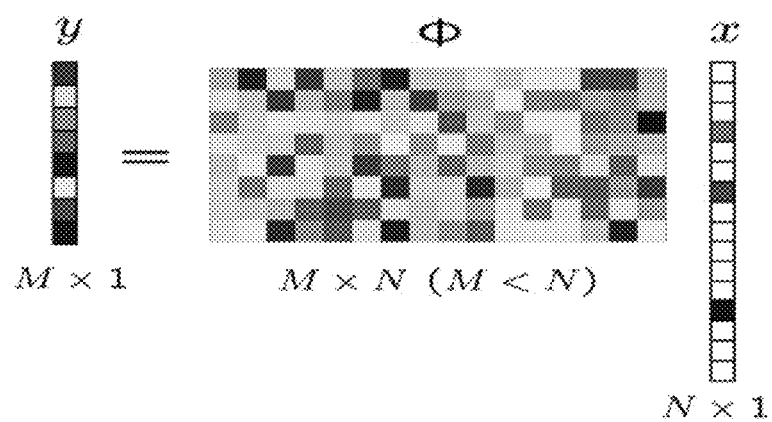
FIG. 14A illustrates a design matrix $\Phi$ for a collection of linear projections.

Suppose the unknown variable is x, a collection of linear projections is represented by design matrix $\Phi$, and measurement is represented by y, as illustrated in FIG. 14A. In the case of radiosurgery, the unknown variable x could describe the properties of the skull, such as, but not limited to, thickness and position. The design matrix $\Phi$ could denote the path of therapeutic beam from different projection angles. Measurement y could be the energy X-ray fluence acquired by the detector 4.

Compressive sensing exploits the fact that the measurement is limited in the space of projections, and tackles the problem by explicitly imposing sparsity promoting regularization in the reconstruction algorithm. The compressive sensing solution can be formulated as the following constrained optimization:

$$\hat{x} = \underset{x}{\operatorname{argmin}} H(x) + J(x) \qquad (1)$$

where the first term is the fidelity term and the second term is the regularization term. The fidelity term is modeled as the square error between reconstructed signal and measurement $H(x)=\|y-\Phi x\|_2^2$. The regularization term takes the form of a sparsity promoting norm. Depending on the property of the anatomy in question, different types of sparsity promoting norms can be used in the optimization. When the convex form of sparsity promoting norm is chosen, both algorithms A and B described below leverage convex optimization techniques.

Model A

The simplest form of sparsity can be modeled as an L1 norm $J(x)=\lambda\|x\|_1$, derived from a Laplacian prior. With such regularization, a Model A algorithm can be obtained, which takes the form:

$$\hat{x} = \underset{x}{\operatorname{argmin}} \|y - \Phi x\|_2^2 + \lambda\|x\|_1 \qquad (2)$$

Since there is no closed-form solution for Model A due to the non-differentiability of the L1 norm, an iterative algorithm, such as, but not limited to, the linearized Bregman algorithm can be used to solve the problem for this model.

Algorithm for Model A

Linearized Bregman Algorithm:

Define Bregman divergence as $D_J^p(u,v)=J(u)-J(v)-\langle p,u-v\rangle$, where p denotes the subgradient of J.

Seek a sequence of solution $\{u^k\}$ in the iterative algorithm, where each subproblem is the solution of the following minimization:

$$x^{k+1} = \operatorname*{argmin}_{x} D_J^{p^k}(x, x^k) + H(x) \qquad (3)$$

In order to solve for this problem more efficiently, a linearization technique can be applied to the fidelity term, $$x^{k+1} = \operatorname*{argmin}_{x} D_J^{p^k}(x, x^k) + \langle \nabla H(x^k), x \rangle + \frac{1}{2\alpha}\|x - x^k\|^2 \qquad (4)$$

and an update for subgradient p is specified based on an optimality condition of the minimization to obtain the linearized Bregman algorithm shown below.

Linearized Bregman Algorithm
Input: $\Phi$, y, J(x), H(x), $\lambda$>0, $\alpha$>0
Algorithm:
Initialize: k=0, $x^0$=0, $p^0$=0
while stopping criteria not satisfied do $$x^{k+1} = \operatorname*{argmin}_{x} D_J^{p^k}(x, x^k) + \langle \nabla H(x^k), x \rangle + \frac{1}{2\alpha}\|x - x^k\|^2 \qquad (5)$$

$$p^{k+1} = p^k - \nabla H(x^k) - \frac{1}{\alpha}(x^{k+1} - x^k) \qquad (6)$$

If $x^{k+1} x^k$, then apply kicking

Update $k=k+1$ (7)

end while
Output: optimal solution $x^k$

In this algorithm, $\lambda$>0 is a regularization parameter that controls the degree of sparsity, $\alpha$>0 is a constant specified by the user, which affects the speed of the algorithm, k=1, ..., n is an integer that indexes the iterate of the algorithm, and $p^k$ is the subgradient on J(x). The regularization parameter $\lambda$ can be determined based on prior knowledge or by cross validation. The linearized Bregman algorithm computes the full regularization path (solution path) corresponding to different levels of sparsity in a computationally efficient manner. The linearized Bregman algorithm has competitive scaling with data dimension, thereby making it an ideal algorithm for large-scale data computation.

Model B

Depending on the structure of the anatomy in question, structured sparsity can also be employed in the regularization term to improve reconstruction. One type of structured sparsity that can be used is total variation (TV), which denotes a semi-norm with bounded variation:

$$TV(x) = \int |\nabla x| \qquad (8)$$

Total variation characterizes an edge of the signal. In the case of bone structures in the skull, since the anatomy is piecewise constant, total variation is suitable since sharp edges are preserved in the reconstruction. Therefore, by using $J(x) = \lambda \int |\nabla x|$ and $H(x) = \|y - \Phi x\|_2^2$, the total variation regularized reconstruction leads to Model B:

$$\hat{x} = \operatorname*{argmin}_{x} \lambda \int |\nabla x| + \|y - \Phi x\|_2^2 \qquad (9)$$

Model B differs from Model A in that it imposes sparsity in the space of edge variation, where (TV) serves as a global operator for preserving edges. Like Model A, there is no closed-form solution for Model B and therefore, an iterative algorithm is used. In order to solve for such a model, the split Bregman algorithm can be used.

Algorithm for Model B
Split Bregman Algorithm:

The split Bregman algorithm splits the energy between the first term J and second term H via variable splitting technique, by introducing another variable u=g(x). The optimization therefore becomes:

$$\operatorname*{argmin}_{x,u} J(u) + H(x) + \frac{\mu}{2}\|u - g(x)\|_2^2 \qquad (10)$$

Solving for a sequence of minimizers is next, where each subproblem solves for:

$$\operatorname*{argmin}_{x,u} D_J^p(u, u^k) + D_H^p(x, x^k) + \frac{\alpha}{2}\|u - g(x)\|_2^2 \qquad (11)$$

The terms J and H are replaced by the associated Bregman divergence respectively.

Split Bregman Algorithm
Input: $\Phi$, y, J(x), H(x), $\lambda$>0, $\alpha$>0
Algorithm:
Initialize: k=0, $x^0$=0, $u^0$=0, $p_x^0$=0, $p_u^0$=0
while stopping criteria not satisfied do $$(x^{k+1}, u^{k+1}) = \qquad (12)$$
$$\operatorname*{argmin}_{x,u} J(u) + H(x) - \langle p_x^k, x - x^k \rangle - \langle p_u^k, u - u^k \rangle + \frac{\alpha}{2}\|u - g(x)\|_2^2$$

$$p_x^{k+1} = p_x^k - \mu \nabla g(x^{k+1})^T (g(x^{k+1}) - u^{k+1}) \qquad (13)$$

$$p_u^{k+1} = p_u^k - \alpha(u^{k+1} - g(x^{k+1})) \qquad (14)$$

Update $k = k + 1$ (15)

end while
Output: optimal solution $x^k$

In this algorithm, $\lambda$>0 is a regularization parameter that controls the degree of sparsity, $\alpha$>0 is a constant specified by the user, which affects the speed of the algorithm, k=1, ..., n is an integer that indexes the iterate of the algorithm, $p_x^k$ is the subgradient on H(x), and $p_u^k$ is the subgradient on J(u). The regularization parameter $\lambda$ can be determined based on prior knowledge or by cross validation. The split Bregman algorithm is synonymous with the Alternating Direction Method of Multipliers (ADMM) method, which is also referred to as the Alternating Direction Augmented Lagrangian (ADAL) method.

For displacement detection, either Model A or Model B can be used to solve for the inverse problem. In either model, the input for the algorithm can be: 1) design matrix $\Phi$, which is constructed by the collection of projection angles and thickness of skull in each projection angles, and 2) measurement y, which is the detected therapeutic fluence. The output of the algorithm can be the estimated thickness of the skull during the treatment, if the anatomy in question is the brain. The choice between Model A and Model B depends on the image quality acquired by the imaging device 30.

Since sensitivity of the therapeutic X-ray detection depends on the variations of the anatomical structures, such as bone and fiducial landmarks, the sensitivity can be further enhanced using contrast agents.

Volume Reconstruction

Figure 14B:
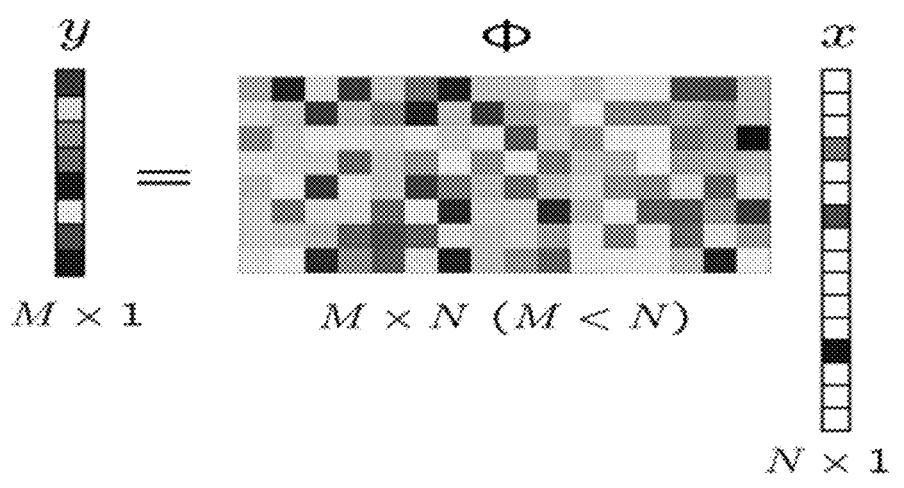

In addition to displacement detection, a 3D volume that is actually targeted by the therapeutic beam can also be reconstructed using reconstruction algorithms included in the computation module (shown in FIG. 11) to be added as a second real-time validation parameter (metric). This additional information can in real-time confirm to an operator that the treatment is being executed as planned. Computational efficiency is the key to real-time 3D target volume reconstruction. Given the limited number of projections for the therapeutic beam and noisy nature of the data, compressive sensing techniques can also be utilized to perform 3D volume reconstruction. For example, suppose the unknown variable is x, a collection of linear projections is represented by design matrix $\Phi$, and measurement is represented by y, as illustrated in FIG. 14B. In the case of radiosurgery, the unknown variable x could be the positions of the target. The design matrix $\Phi$ could denote the collection of X-ray projections. Measurement y could be the detected therapeutic energy. Specifically, for volume reconstruction, the geometry of the therapeutic beam projections can be formulated as the design matrix $\Phi$, while the transmitted X-ray fluence as observations y. The explanatory variables x that are sought are the positions of the target.

Compressive sensing exploits the fact that the measurement is limited in the space of projections, and tackles the problem by explicitly imposing sparsity promoting regularization in the reconstruction algorithm. The compressive sensing solution can be formulated as the following constrained optimization:

$$\hat{x} = \arg\min_x H(x) + J(x) \tag{16}$$

where the first term is the fidelity term and the second term is the regularization term. The fidelity term is modeled as the square error between reconstructed signal and measurement $H(x)=\|y-\Phi x\|_2^2$. The regularization term takes the form of a sparsity promoting norm. Depending on the property of the anatomy in question, different types of sparsity promoting norms can be used in the optimization. When the convex form of sparsity promoting norm is chosen, both algorithms A and B described below leverage convex optimization techniques.

Model A

The simplest form of sparsity can be modeled as an L1 norm $J(x)=\lambda\|x\|_1$, derived from a Laplacian prior. With such regularization, a Model A algorithm can be obtained, which takes the form:

$$\hat{x} = \arg\min_x \|y - \Phi x\|_2^2 + \lambda\|x\|_1 \tag{17}$$

Since there is no closed-form solution for Model A due to the non-differentiability of the L1 norm, an iterative algorithm, such as, but not limited to, the linearized Bregman algorithm can be used to solve the problem for this model.

Algorithm for Model A

Linearized Bregman Algorithm:

Define Bregman divergence as $D_f^p(u,v)=J(u)-J(v)-\langle p, u-v\rangle$, where p denotes the subgradient of J.

Seek a sequence of solution $\{u^k\}$ in the iterative algorithm, where each subproblem is the solution of the following minimization:

$$x^{k+1} = \arg\min_x D_J^{p^k}(x, x^k) + H(x) \tag{18}$$

In order to solve for this problem more efficiently, a linearization technique is applied to the fidelity term, $$x^{k+1} = \arg\min_x D_J^{p^k}(x, x^k) + \langle \nabla H(x^k), x\rangle + \frac{1}{2\alpha}\|x - x^k\|^2 \tag{19}$$

and an update for subgradient p is specified based on an optimality condition of the minimization to obtain the linearized Bregman algorithm shown below.

Linearized Bregman Algorithm

Input: $\Phi$, y, J(x), H(x), $\lambda>0$, $\alpha>0$

Algorithm:

Initialize: k=0, $x^0=0$, $p^0=0$ while stopping criteria not satisfied do $$x^{k+1} = \arg\min_x D_J^{p^k}(x, x^k) + \langle \nabla H(x^k), x\rangle + \frac{1}{2\alpha}\|x - x^k\|^2 \tag{20}$$

$$p^{k+1} = p^k - \nabla H(x^k) - \frac{1}{\alpha}(x^{k+1} - x^k) \tag{21}$$

If $x^{k+1}=x^k$, then apply kicking

Update k=k+1 (22)

end while

Output: optimal solution $x^k$

In this algorithm, $\lambda>0$ is a regularization parameter that controls the degree of sparsity, $\alpha>0$ is a constant specified by the user, which affects the speed of the algorithm, k=1, . . . , n is an integer that indexes the iterate of the algorithm, and $p^k$ is the subgradient on J(x).

Model B

Depending on the structure of the anatomy in question, structured sparsity can also be employed in the regularization term to improve reconstruction. One type of structured sparsity that can be used is total variation (TV), which denotes a semi-norm with bounded variation:

$$TV(x)=\int|\nabla x| \tag{23}$$

Total variation characterizes an edge of the signal. In the case of bone structures in the skull, since the anatomy is piecewise constant, total variation is suitable since sharp edges are preserved in the reconstruction. Therefore, by using $J(x)=\lambda\int|x|$ and $H(x)=\|y-\Phi x\|_2^2$, the total variation regularized reconstruction leads to Model B:

$$\hat{x} = \arg\min_x \lambda\int|\nabla x| + \|y - \Phi x\|_2^2 \tag{24}$$

Model B differs from Model A in that it imposes sparsity in the space of edge variation, where (TV) serves as a global operator for preserving edges. Like Model A, there is no closed-form solution for Model B and therefore, an iterative algorithm is used. In order to solve for such a model, the split Bregman algorithm can be used.

Algorithm for Model B
Split Bregman Algorithm:
The split Bregman algorithm splits the energy between the first term J and second term H via variable splitting technique, by introducing another variable u=g(x). The optimization therefore becomes:

$$\underset{x,u}{\mathrm{argmin}} J(u) + H(x) + \frac{\mu}{2}\|u - g(x)\|_2^2 \tag{25}$$

Solving for a sequence of minimizers is next, where each subproblem solves for:

$$\underset{x,u}{\mathrm{argmin}} D_J^p(u, u^k) + D_H^p(x, x^k) + \frac{\alpha}{2}\|u - g(x)\|_2^2 \tag{26}$$

The terms J and H are replaced by the associated Bregman divergence respectively.
Split Bregman Algorithm
Input: $\Phi$, y, J(x), H(x), $\lambda$>0, $\alpha$>0
Algorithm:
Initialize: k=0, $x^0$=0, $u^0$=0, $p_x^0$=0, $p_u^0$=0
while stopping criteria not satisfied do $$(x^{k+1}, u^{k+1}) = \tag{27}$$
$$\underset{x,u}{\mathrm{argmin}} J(u) + H(x) - \langle p_x^k, x - x^k\rangle - \langle p_u^k, u - u^k\rangle + \frac{\alpha}{2}\|u - g(x)\|_2^2$$

$$p_x^{k+1} = p_x^k - \mu \nabla g(x^{k+1})^T(g(x^{k+1}) - u^{k+1}) \tag{28}$$

$$p_u^{k+1} = p_u^k - \alpha(u^{k+1} - g(x^{k+1})) \tag{29}$$

Update $k=k+1$ (30)

end while
Output: optimal solution $x^k$

In this algorithm, $\lambda$>0 is a regularization parameter that controls the degree of sparsity, $\alpha$>0 is a constant specified by the user, which affects the speed of the algorithm, k=1, ..., n is an integer that indexes the iterate of the algorithm, $p_x^k$ is the subgradient on H(x), and $p_u^k$ is the subgradient on J(u).

As a regression problem, the sparse nature of projections can be exploited, and L1 regularization as part of the optimization objective can be used. Computationally efficient and accurate algorithms as shown above via convex optimization can also be used. Structured sparsity such as Total Variation (TV) can be employed as a regularization form during the reconstruction, if the target profile is piece-wise constant. Model A or Model B can be used to perform the 3D volume reconstruction. The input of the algorithm can include: 1) design matrix $\Phi$, which is the collection of projections, and 2) measurement y, which is the detected therapeutic energy. The output of the algorithm can include the 3D volume of therapeutic energy distribution.

Figure 8C:
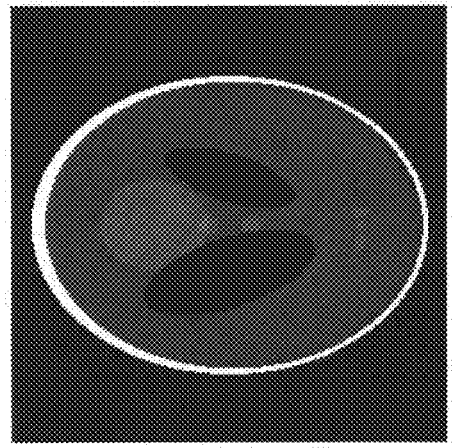
FIGS. 8A-8C show differences between different image reconstruction methods.
Figure 8B:
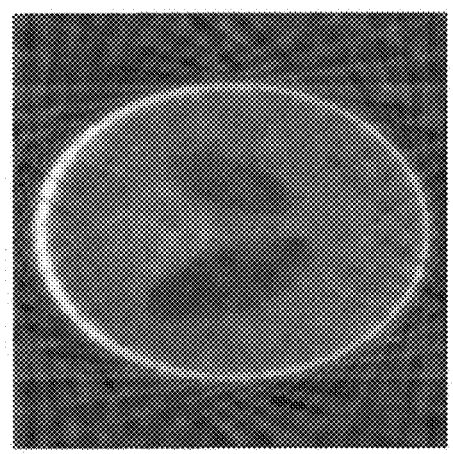
Figure 8A:
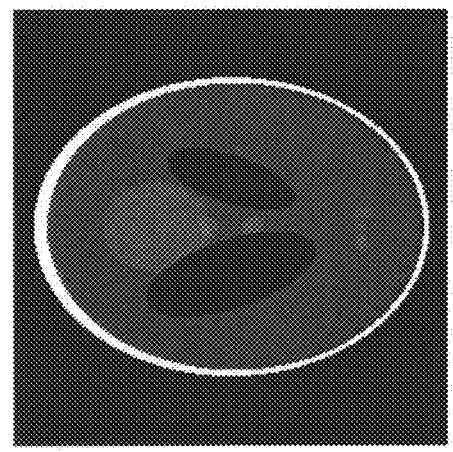

In contrast to filtered back projection algorithms used in traditional CT reconstruction, compressive sensing algorithms are associated with an iterative method and need fewer projections to reconstruct the volume. As shown in FIGS. 8A-8C, even with fewer number of projection angles, compressive sensing leads to a better image reconstruction than the filtered back projection. Sparsity promoting norms are key to the compressive sensing algorithm, because they exploit prior information in the observations to improve reconstruction. The algorithm is iterative in nature. In each iteration, the system 100 evaluates the residual reconstruction error, and uses the algorithm to update the current iteration. Convex relaxation of sparsity promoting norms can also be used as regularizations, and therefore convex optimization techniques can be used to solve for Models A and B. When the regularization takes the form of L1 norm, the linearized Bregman algorithm can be used to solve for it. When the regularization takes the form of Total Variation semi-norm, the split Bregman algorithm can be used.

If the reconstruction is very good compared to the normal environment, the threshold for generating an alarm signal when a displacement is present can have a first value. If the reconstruction is not very good, for example, when the number of samples is very low or when the projection angles are too coherent, a different, second threshold value can be set for generating an alarm signal in case of a displacement.

Theoretical Guarantees

The quality of the 3D volume reconstruction depends on the number of projections and geometry of the radiation therapy device. Theoretical guarantees can also be derived, and statistical simulations can be performed to determine the minimum number of projections required to achieve volume reconstruction of sufficient quality. The minimum number of projections will depend on how sparse the anatomy in question is and how many unknown variables are present. For a linear system, such as in Model A, if the measurement is randomly sampled, the anatomy is k-sparse, the dimension of unknown variables is n, then the minimum number of samples can be:

$$m \geq Ck \log(n/k) \tag{31}$$

where C is a constant. A variant of such guarantee can be explored with respect to the specific detector 4 design, since the geometry of the problem poses constraints on the randomness of measurement, and thus offers different bounds. Due to the local operator used in the reconstruction algorithm, the nature of the computation can be parallel. Thus, parallel computing architectures such as GPU can be used to accelerate the computations.

Dosimetry

In addition to the real-time correlation and 3D actual target volume reconstruction steps, the radiation dose delivered to the target can also be computed in real-time and added as a third real-time target validation parameter (metric).

During the treatment, the radiation detector 4 in the imaging device 30 collects radiation projection data. The radiation dose calculation module (shown in FIG. 12) includes computational algorithms configured to extract both the shape and dose distribution from the collected in-treatment images and to compare this information with the library of predicted radiation doses stored in the computer 50. In intensity modulated treatment therapies, additional information regarding the variation in the shape of the therapeutic beam based on the different projection angles, and even different time points, can also be used. The combination of the shape and dose distribution information helps to determine whether any inconsistency in the actual treatment dose delivered is due to incorrect dose delivery or the target displacement. The radiation calculation module calculates the total dose delivered over the entire surgery as a metric. During the treatment, the system 100 can continuously compare the actual delivered radiation dose with the prescribed dose. If the delivered dose is significantly different from the prescribed dose, under certain statistical criterion, a feedback signal can be sent to the controller 40 to interrupt the radiosurgery or radiation treatment therapy. A dose evaluation method as described in U.S. application Ser. No. 13/650,980, filed Oct. 12, 2012, titled "SYSTEMS, DEVICES, AND METHODS FOR QUALITY ASSURANCE OF RADIATION THERAPY", the content of which is incorporated herein by reference in its entirety, can be used to quantitatively evaluate the differences between the measured and the predicted dose distributions.

Closed-Loop Feedback

If a displacement of the target is detected, the analysis module sends a closed-loop feedback signal to the linear accelerator controller 40 to stop radiation treatment and/or to allow the surgeon to adjust the delivery of the radiation therapy treatment during the therapy session. The system 100 can perform this function based on instructions provided in the computation module to determine the displacement. This can also be done by combining the displacement information obtained from the correlation and the actual 3D target volume reconstruction steps with the dosimetry information in the dosimeter monitoring step. If it is determined by the analysis module that the displacement is outside a predetermined threshold range, a feedback module generates a feedback signal which is sent to the controller 40, thereby allowing the surgeon to stop the surgery during the treatment and recalibrate the radiation therapy/radiosurgery device 10. Additional information obtained from a (keV) X-ray imaging device (not shown), which can be turned on during the treatment, can augment this process and improve displacement detection.

Recalibration

In addition to the stop signal, which is a binary decision signal, an additional parameter (metric) can be computed to guide the recalibration process. A repositioning signal is helpful for the surgeon to determine where and how to place the patient 5 with respect to the isocenter of radiation inside the radiation radiosurgery device 10, after stopping for recalibration. Given the library of DRRs computed and stored prior to treatment, and the collected live therapeutic in-treatment images acquired for displacement detection, a gradient field of signal change can be computed. A search direction can be optimized to seek the direction of the displacement in order to maximize the correlation between the in-treatment projection images and the DRRs. Since the displacement of the patient 5 is relatively small for radiosurgeries, it can be assumed that the perturbations are linear and that a unique maximum exists for the correlation landscape. In doing so, the adjustment and the direction of the adjustment can be determined during the recalibration process.

For example, given a span of isocenters, a library of DRR images for each angle can be simulated. This is denoted by $L(i,j,k)$, where $(i,j,k)$ denotes the coordinate for isocenters, $i=1\ldots n, j=1\ldots n, k=1\ldots n$. In other words, a collection of DRR images based on a 3D grid of all possible isocenters is obtained. During the treatment, an image is acquired using the therapeutic imaging device 30 for that same angle, denoted by $I(i_c, j_c, k_c)$. The correlation between the $I(x_o, y_o, z_o)$ and each image in the DRR library can be computed using:

$$C(i,j,k) = \text{corr}(L(i,j,k), I(i_c, j_c, k_c)) \quad (32)$$

A gradient field can be computed based on a correlation map:

$$g = (g_x, g_y, g_z) = \left(\frac{\partial C}{\partial x}, \frac{\partial C}{\partial y}, \frac{\partial C}{\partial z}\right) \quad (33)$$

Once a displacement signal is detected, the direction to mitigate the displacement can be determined by going in the opposite direction as the gradient field. To minimize the correlation, an estimate of the step size to be taken can be computed using:

$$(dx, dy, dz) = \arg\min_{dx,dy,dz} C(i, j, k) - \langle (g_x, g_y, g_z), (dx, dy, dz) \rangle \quad (34)$$

When a step size and direction are computed, they can be sent as feedback to the controller 40 for the linear accelerator 2 to close the loop. This information act as a fourth metric and can assist the surgeon to recalibrate the device 10 and to adjust the aim of the therapeutic beam.

Figure 9:
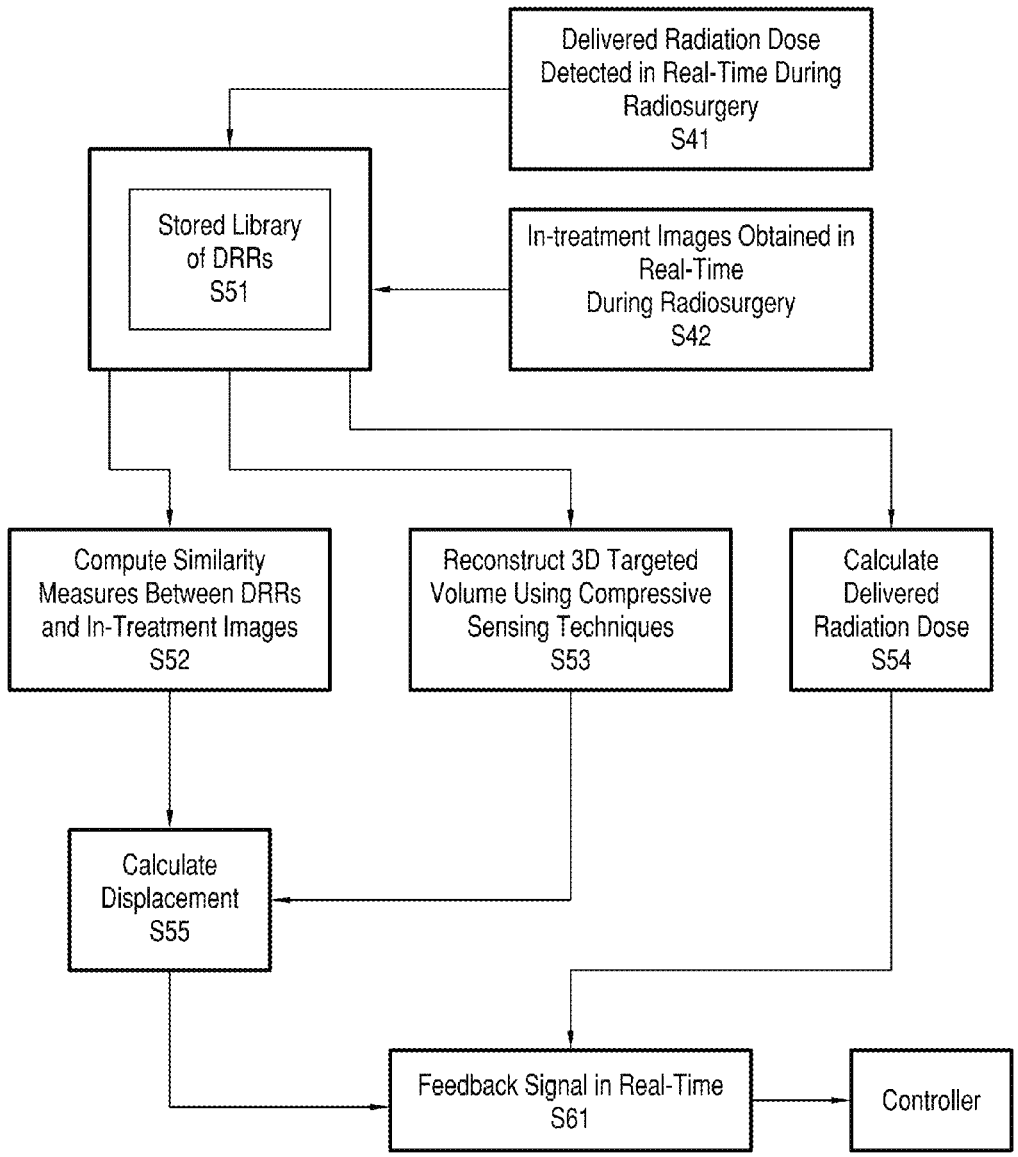
FIG. 9 is a flow chart of a real-time target validation method according to various embodiments.
Figure 10:
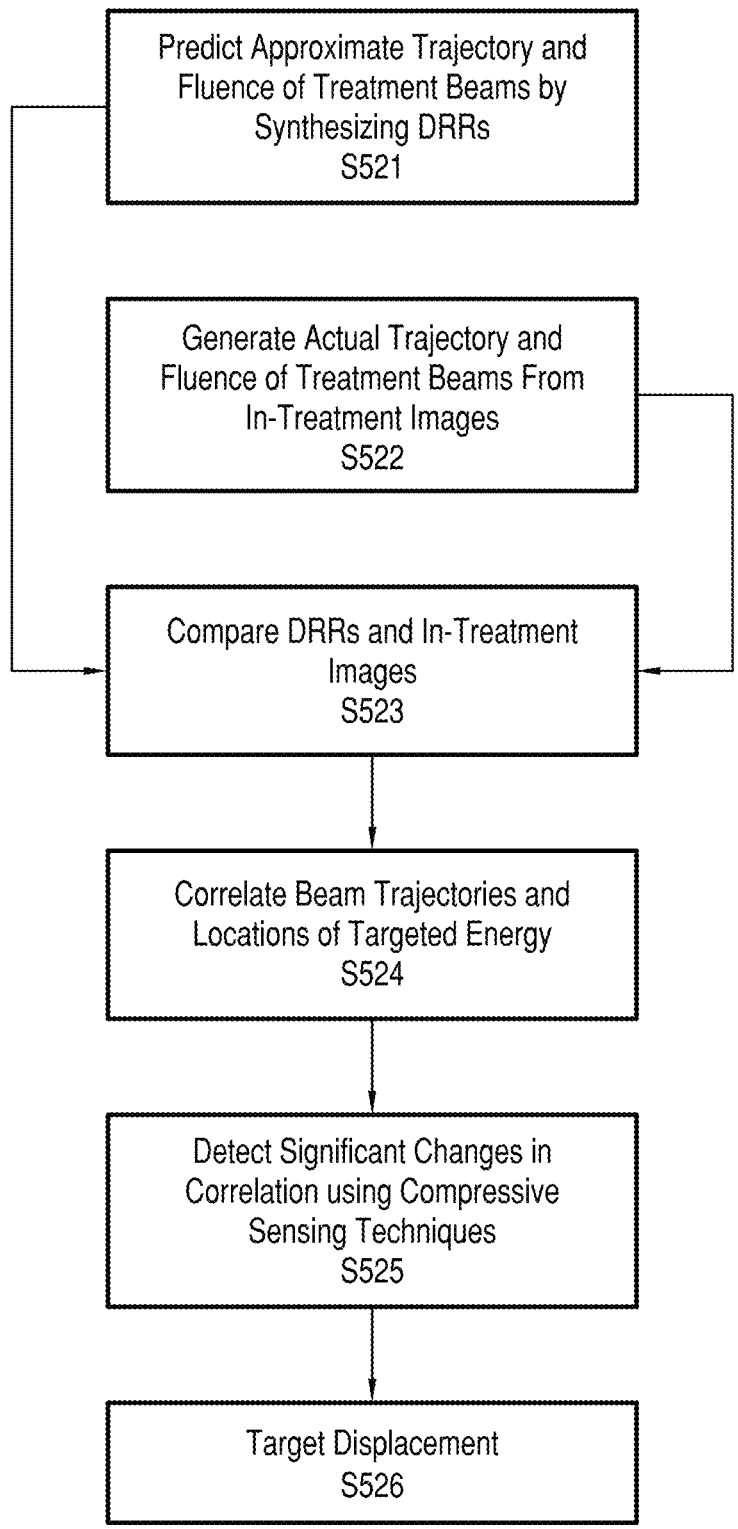
FIG. 10 is a flow chart of a method to determine target displacement according to various embodiments.
Figure 11:
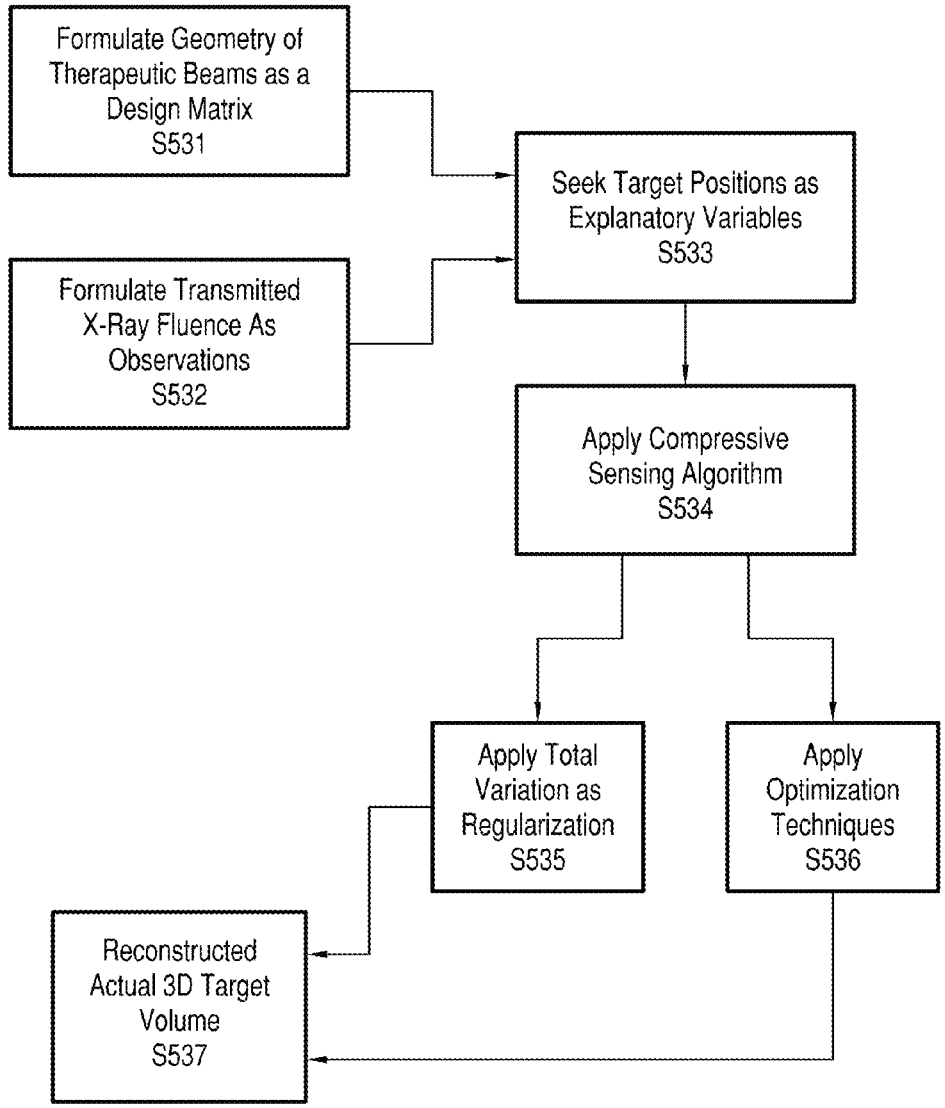
FIG. 11 is a flow chart of a method to reconstruct an actual 3D target volume according to various embodiments.

The real-time target validation process steps are shown in FIGS. 9-11. During radiation treatment, in-treatment images are generated in S42 by the digital imaging device 30. Also, in S41 the radiation detector 4 detects the radiation dose delivered to the target. The live in-treatment images and the dosimeter information are sent in S51 to the computer 50 for processing. Using compressive sensing techniques, as discussed hereinabove, for example, in real-time, the computer 50, in parallel, computes similarity measurements between the live images and the previously generated DRRs in S52, reconstructs the 3D targeted volume in S53, and calculates the delivered radiation dose in S54. The system then computes a displacement measurement signal in S55, and upon determination that the displacement measurement signal is larger than a threshold signal, transmits a feedback signal in S61 to the controller 40 to either automatically stop the radiation treatment or to allow a medical personnel to stop the treatment.

The similarity measurement computation, according to various embodiments, is shown in FIG. 10. In Step S521, prior to radiation treatment, the system 100 predicts the approximate trajectory and X-ray fluence of the treatment beams by synthesizing DRRs. Upon receiving the in-treatment live images, the system 100 generates actual trajectory and fluence of treatment beams from the live in-treatment images in S522 and compares in S523 and correlates in S524 in real-time the beam trajectories and locations of targeted energies of the two sets of images. Using compressive sensing techniques as discussed herein, the system 100 detects in S525 whether there are significant changes in the correlation and computes a target displacement in S526.

The 3D actual target volume reconstruction is shown in FIG. 11. Using parallel computing techniques, while the similarity measures are computed, as shown in FIG. 10, the system 100 can also use compressive sensing techniques as discussed herein to formulate the geometry of the therapeutic beams as a design matrix in S531, the transmitted X-ray fluences as observations in S532, and the sought target positions as explanatory variables in S533. Using compressive sensing techniques as discussed previously, in S534 together with the application of total variation as regularization in S535 and optimization techniques in S536, the system 100 in S537 reconstructs the actual 3D target volume. If there is a difference between the actual 3D target volume and the planned 3D target volume, a displacement is registered and a feedback signal is generated, as shown in FIG. 9.

A non-transitory computer readable medium can be used to store the software or programmed instructions and data which when executed by a computer processing system 50 causes the system to perform various methods of the present invention, as discussed herein. The executable software and data may be stored in various places, including, for example, the memory and storage of the computer processing system 50 or any other device that is capable of storing software and/or data.

Accordingly, embodiments of real-time target validation systems, methods and computer program products have been disclosed. Many alternatives, modifications, and variations are enabled by the present disclosure. Features of the disclosed embodiments can be combined, rearranged, omitted, etc. within the scope of the invention to produce additional embodiments.

Further, a method of adjusting further administration of a therapeutic radiation beam to a target during a radiation treatment session is also disclosed, the adjusting being performed based on a determination made during the treatment session that there is a change in a parameter of the target, the determination being performed based on target projection images continually generated during the treatment using the therapeutic radiation beam.

Also, a non-transitory computer-readable storage medium is disclosed upon which is embodied a sequence of programmed instructions for validating in real-time a target exposed to radiation therapy in a radiation therapy treatment system including a computer processing system which executes the sequence of programmed instructions embodied on the computer-readable storage medium to cause the computer processing system to perform the steps of: comparing X-ray images of a target volume obtained during treatment using a therapeutic radiation beam with a corresponding previously obtained 2D projections of the target volume; determining similarity measures between the X-ray images and the reference images; detecting a displacement of the target volume based on the similarity measures; comparing the displacement with a threshold displacement; and generating a feedback signal if the displacement exceeds the threshold displacement.

Further, systems and methods of adjusting further administration of a therapeutic radiation beam to a target during a radiation treatment session based on a determination made during the treatment session of a change in a parameter of the target, the determination being performed based on target projection images continually generated during the treatment using the therapeutic radiation beam, are also disclosed.

Furthermore, certain features of the disclosed embodiments may sometimes be used to advantage without a corresponding use of other features. Accordingly, Applicants intend to embrace all such alternatives, modifications, equivalents, and variations that are within the spirit and scope of the present disclosure.

While embodiments and applications of this invention have been shown and described, it would be apparent to those skilled in the art that many more modifications are possible without departing from the inventive concepts herein. The invention is not limited to the description of the embodiments contained herein, but rather is defined by the claims appended hereto and their equivalents.

What is claimed is:

1. A method of validating a target during a radiation therapy treatment session, comprising:
generating X-ray images of a target volume using the therapeutic radiation beam;
comparing the X-ray images of the target volume with corresponding previously generated reference images of a 3D scan of the target volume to determine similarity measures between the X-ray images and the reference images, the similarity measures comprising a measure of similarity between the radiation beam trajectories in the X-ray images and corresponding reference images and a measure of similarity between locations of the radiation beam energies in the X-ray images and corresponding reference images; and
determining a displacement of the target volume based on the similarity measures,
wherein when the displacement exceeds a threshold displacement a feedback signal is generated.

2. The method of claim 1, further comprising:
reconstructing a 3D target volume using the X-ray images, and determining a displacement of the target volume based on the similarity measures and the reconstructed 3D target volume.

3. The method of claim 1, further comprising determining in real-time a radiation dose delivered to the target volume.

4. The method of claim 3, wherein determining the displacement includes determining the displacement of the target volume based on the similarity measures, and the radiation dose delivered to the target volume.

5. The method of claim 1, wherein the comparing includes comparing X-ray trajectory and energy information contained in the X-ray images with corresponding trajectory and energy information contained in the reference images.

6. The method of claim 1, wherein the reference images are synthetic digitally reconstructed radiographs (DRRs).

7. The method of claim 6, wherein the DRRs are generated by simulating projections of the X-rays at a target volume at different isocenters of radiation and different projection angles using ray tracking simulation approximation models.

8. The method of claim 1, further comprising determining a change in the similarity measure using a compressive sensing technique.

9. The method of claim 8, wherein the compressing sensing technique includes computing a solution path corresponding to different sparsity levels.

10. The method of claim 9, wherein the computing includes applying a linearized Bregman algorithm or a split Bregman algorithm.

11. The method of claim 8, wherein the compressive sensing technique uses a minimum number of X-ray projection images to determine the change in the similarity measure.

12. The method of claim 8, wherein a change in the similarity measure larger than a predetermined change indicates a displacement of the target volume.

13. The method of claim 2, wherein the reconstructing includes reconstructing in real-time the 3D target volume using a compressive sensing technique.

14. The method of claim 13, wherein the compressive sensing technique uses a previously determined minimum number of X-ray projection images.

15. The method of claim 2, further comprising validating a spatial position and orientation of the target volume based on the reconstructed 3D target volume.

16. The method of claim 1, wherein the radiation therapy treatment is radiosurgery.

17. The method of claim 1, wherein the feedback signal generated is indicating a request to stop the treatment.

18. A non-transitory computer-readable storage medium upon which is embodied a sequence of programmed instructions for validating in real-time a target exposed to radiation therapy in a radiation therapy treatment system including a computer processing system which executes the sequence of programmed instructions embodied on the computer-readable storage medium to cause the computer processing system to perform the steps of:
  comparing X-ray images of a target volume obtained during treatment using a therapeutic radiation beam with a corresponding previously obtained 2D projections of the target volume;
  determining similarity measures between the X-ray images and the reference images, the similarity measures comprising a measure of similarity between the radiation beam trajectories in the X-ray images and corresponding reference images and a measure of similarity between locations of the radiation beam energies in the X-ray images and corresponding reference images;
  detecting a displacement of the target volume based on the similarity measures; and
  generating a feedback signal if the displacement exceeds a threshold displacement.

19. The non-transitory computer-readable medium of claim 18, further comprising reconstructing a 3D target volume using the X-ray images, and detecting a displacement of the target volume based on the similarity measures and the reconstructed 3D target volume.

20. The non-transitory computer-readable storage medium of claim 18, further comprising:
  determining in real-time a radiation dose delivered to the target volume; and
  detecting a displacement of the target volume based on the similarity measures, the reconstructed 3D target volume, and the radiation dose delivered to the target volume.

21. The non-transitory computer-readable storage medium of claim 18, further comprising stopping the radiation treatment using the feedback signal.

22. The non-transitory computer-readable storage medium of claim 18, further comprising:
  comparing X-ray trajectory and energy information from the X-ray images with corresponding trajectory and energy information from the reference images.

23. The non-transitory computer-readable storage medium of claim 18, further comprising determining changes in the similarity measures using a compressive sensing technique.

24. The non-transitory computer-readable storage medium of claim 23, wherein the compressive sensing technique uses a minimum number of X-ray projection images to determine the changes in the similarity measures.

25. The non-transitory computer-readable storage medium of claim 19, further comprising determining a minimum number of X-ray projection images needed to reconstruct the 3D target volume.

26. The non-transitory computer-readable storage medium of claim 25, further comprising reconstructing the 3D volume using a compressive sensing technique, wherein the compressive sensing technique uses the minimum number of X-ray projection images.

27. The non-transitory computer-readable storage medium of claim 26, further comprising optimization and regularization enhancing algorithms to increase accuracy of the compressive sensing technique.

28. The non-transitory computer-readable storage medium of claim 19, further comprising validating a spatial position and orientation of the target volume based on the reconstructed 3D target volume.

29. The non-transitory computer-readable storage medium of claim 18, wherein the radiation therapy treatment system is an image-guided radiosurgery system.

30. A method of validating a target in real-time during radiosurgery, comprising:
  generating X-ray projection images of a target volume using the therapeutic X-ray beam;
  comparing the set of X-ray projection images with corresponding previously generated reference images of 2D projections of the target volume;
  determining a similarity measure between an X-ray image and a corresponding reference image, the similarity measure comprising a measure of similarity between the radiation beam trajectories in the X-ray image and the corresponding reference image and a measure of similarity between locations of the radiation beam energies in the X-ray image and the corresponding reference image; and
  determining a displacement of the target volume based on the similarity measure,
  wherein when the displacement exceeds the threshold displacement a feedback signal is generated.

31. The method of claim 30, further comprising reconstructing a 3D target volume using the X-ray projection images.

32. The method of claim 31, further comprising determining a displacement of the target volume based on the similarity measure and the reconstructed 3D target volume.

33. The method of claim 31, further comprising:
  determining prior to radiation therapy treatment the minimum X-ray projection images needed to determine the similarity measure and to reconstruct the 3D target volume.

34. The method of claim 33, wherein the determining of the similarity measure and the reconstructing of the 3D target volume uses compressive sensing techniques.

35. The method of claim 31, further comprising:
  determining a radiation dose delivered to the target volume; and
  determining the displacement of the target volume based on the similarity measure, the reconstructed 3D target volume, and the radiation dose delivered to the target volume.

36. The method of claim 31, further comprising validating in real-time a spatial position and orientation of the target volume based on the reconstructed 3D target volume.

37. The method of claim 30, wherein the X-ray projection images are generated using a digital imaging device.

38. The method of claim 37, wherein the digital imaging device includes one of a CMOs detector, an amorphous silicon detector, a segmented ion chamber, a multiwire proportional counter, scintillating fibers, and Cerenkov detectors.

39. An image-guided radiation therapy system, comprising:
  a digital imaging detector to generate a series of X-ray projection images of a target volume exposed to therapeutic radiation;
  a computer processing system configured to validate the target in real-time, the computer processing system including a non-transitory computer-readable storage medium upon which is embodied a sequence of programmed instructions which when executed by the computer processing system executes the sequence of programmed instructions to cause the computer processing system to:

compare the X-ray images of the target volume with a corresponding previously obtained reference images of 2D projections of the target volume;

determine similarity measures between the X-ray images and the reference images, the similarity measures including a measure of similarity between the radiation beam trajectories in the X-ray images and corresponding reference images and a measure of similarity between locations of the radiation beam energies in the X-ray images and corresponding reference images;

reconstruct a 3D target volume using the X-ray images;

determine a displacement of the target volume based on the similarity measures and the reconstructed 3D target volume; and generate a feedback signal if the displacement exceeds a threshold displacement;

the system further comprising a controller to stop the radiation treatment upon receipt of the feedback signal.

40. The system of claim 39, wherein the reference images are synthetic digitally reconstructed radiographs (DRRs) stored as a library of images in a storage device in the computer processing system.

41. The method of claim 40, wherein the DRRs are generated by simulating projections of the X-rays at a target volume at different isocenters of radiation and different projection angles using ray tracking simulation approximation models.

42. The system of claim 39, wherein the reconstruction of the 3D target volume and the determining of the displacement is by using compressive sensing techniques.

43. The system of claim 39, further comprising detecting in real-time a radiation dose delivered to the target volume, wherein the determining the displacement of the target volume is based on the similarity measures, the reconstructed 3D target volume, and the radiation dose delivered to the target volume.

44. A method of adjusting further administration of a therapeutic radiation beam to a target during a radiation treatment session based on a determination made during the treatment session of a change in a parameter of the target, the determination being performed based on a comparison between target projection images continually generated during the treatment using the therapeutic radiation beam and corresponding reference images, wherein the parameter comprises a similarity measure between radiation beam trajectories in the target projection images and corresponding reference images and between radiation beam energies deposited in the target projection images and corresponding reference images.

45. The method of claim 44, wherein the parameter further includes a target spatial position and orientation, and radiation dose.

46. The method of claim 44, wherein the determination includes comparing the target projection images with corresponding previously obtained projection images and computing similarity measures between the images using a compressive sensing computation algorithm.

47. The method of claim 46, wherein the compressive sensing computation algorithm includes a linearized Bregman algorithm or a split Bregman algorithm.

48. The method of claim 47, wherein the comparing and computing are continually performed during the treatment session.

49. The method of claim 48, further comprising generating a feedback signal upon determining a change in the parameter, wherein the adjustment is made in response to the feedback signal.

* * * * *